US012773241B2

(12) United States Patent
Whittaker et al.

(10) Patent No.: US 12,773,241 B2
(45) Date of Patent: Oct. 27, 2026

(54) FIXATION DEVICES AND ASSOCIATED SYSTEMS AND METHODS

(71) Applicant: Curvafix, Inc., Bellevue, WA (US)

(72) Inventors: Eric Whittaker, Edmonds, WA (US); Blake Matsuzaki, Bothell, WA (US); Carly Anderson Thaler, Seattle, WA (US); Nathan Dale, San Diego, CA (US); Steven Dimmer, Bellevue, WA (US)

(73) Assignee: Curvafix, Inc., Bellevue, WA (US)

( * ) Notice: Subject to any disclaimer, the term of this patent is extended or adjusted under 35 U.S.C. 154(b) by 321 days.

(21) Appl. No.: 18/338,850

(22) Filed: Jun. 21, 2023

(65) Prior Publication Data

US 2023/0404636 A1 Dec. 21, 2023

Related U.S. Application Data

(60) Provisional application No. 63/366,724, filed on Jun. 21, 2022.

(51) Int. Cl.

*A61B 17/72* (2006.01)
*A61B 17/88* (2006.01)
*A61B 17/17* (2006.01)

(52) U.S. Cl.

CPC ........ *A61B 17/725* (2013.01); *A61B 17/7208* (2013.01); *A61B 17/8872* (2013.01); *A61B 17/1725* (2013.01)

(58) Field of Classification Search

CPC .... A61B 17/72; A61B 17/725; A61B 17/7208
See application file for complete search history.

(56) References Cited

U.S. PATENT DOCUMENTS 2,328,270 A 8/1943 Daniel
2,724,573 A 11/1955 Lundquist
3,371,725 A 3/1968 Wilhelm et al.
(Continued)

FOREIGN PATENT DOCUMENTS

AT 509852 A4 12/2011
AT 509852 B1 12/2011
(Continued)

OTHER PUBLICATIONS

US 7,273,482 B2, 09/2007, Dakin et al. (withdrawn)
(Continued)

*Primary Examiner* — Tessa M Matthews
(74) *Attorney, Agent, or Firm* — Fortem IP LLP

(57) ABSTRACT

The present technology may comprise a fixation device. The fixation device can comprise an elongate body comprising a plurality of interconnected segments, each of the segments comprising an engagement member, a recess configured to receive the engagement member of an adjacent one of the segments, and a plurality of channels. At least one of the channels can extend through the engagement member. The fixation device can further comprise a plurality of flexible elongate members, each extending through one of the channels. The elongate body can be transformable between a flexible configuration in which the elongate members can move relative to one another and a rigid configuration in which the elongate members are fixed relative to one another.

35 Claims, 14 Drawing Sheets

(56) References Cited

U.S. PATENT DOCUMENTS

| | | | |
|---|---|---|---|
| 4,098,351 | A | 7/1978 | Alessio |
| 4,489,792 | A | 12/1984 | Fahim et al. |
| 4,491,443 | A | 1/1985 | Decaro |
| 4,605,348 | A | 8/1986 | Decaro |
| 4,706,659 | A | 11/1987 | Matthews et al. |
| 5,108,397 | A | 4/1992 | White |
| 5,167,665 | A | 12/1992 | McKinney |
| 5,234,435 | A | 8/1993 | Seagrave |
| D346,218 | S | 4/1994 | White |
| 5,300,071 | A | 4/1994 | Browner et al. |
| 5,336,224 | A | 8/1994 | Selman |
| 5,527,309 | A | 6/1996 | Shelton |
| 5,527,310 | A | 6/1996 | Cole et al. |
| 5,593,407 | A | 1/1997 | Reis |
| 5,601,550 | A | 2/1997 | Esser |
| 5,649,925 | A | 7/1997 | Barbera |
| 5,879,352 | A | 3/1999 | Filoso et al. |
| 5,944,719 | A | 8/1999 | Leban |
| 5,993,454 | A | 11/1999 | Longo |
| 6,209,886 | B1 | 4/2001 | Estes et al. |
| 6,340,362 | B1 | 1/2002 | Pierer et al. |
| 6,368,326 | B1 | 4/2002 | Dakin et al. |
| 7,258,692 | B2 | 8/2007 | Thelen et al. |
| 7,410,483 | B2 | 8/2008 | Danitz et al. |
| 7,410,489 | B2 | 8/2008 | Dakin et al. |
| 7,625,395 | B2 | 12/2009 | Mueckter |
| 7,632,277 | B2 | 12/2009 | Woll et al. |
| 7,785,325 | B1 | 8/2010 | Milbank |
| 7,846,162 | B2 | 12/2010 | Nelson et al. |
| 8,043,347 | B2 | 10/2011 | Jiang et al. |
| 8,128,626 | B2 | 3/2012 | Justin |
| 8,128,627 | B2 | 3/2012 | Justin et al. |
| 8,157,803 | B1 | 4/2012 | Zirkle et al. |
| 8,206,389 | B2 | 6/2012 | Huebner et al. |
| 8,372,074 | B2 | 2/2013 | Milbank |
| 8,409,257 | B2 | 4/2013 | Edidin et al. |
| 8,439,916 | B2 | 5/2013 | Coati et al. |
| 8,632,543 | B2 | 1/2014 | Metzinger et al. |
| 8,961,516 | B2 | 2/2015 | Nelson et al. |
| 9,060,809 | B2 | 6/2015 | Tipirneni et al. |
| 9,144,506 | B2 | 9/2015 | Phelps |
| 9,155,574 | B2 | 10/2015 | Saravia et al. |
| 9,482,260 | B1 | 11/2016 | Krause |
| 9,498,264 | B2 | 11/2016 | Harshman et al. |
| 9,532,789 | B2 | 1/2017 | Coope |
| 9,615,835 | B2 | 4/2017 | Lam et al. |
| 9,839,435 | B2 | 12/2017 | Meek et al. |
| 10,258,394 | B2 | 4/2019 | Harshman et al. |
| 10,307,188 | B2 | 6/2019 | Harshman et al. |
| 10,973,559 | B2 | 4/2021 | Harshman et al. |
| 11,224,467 | B2 | 1/2022 | Peterson et al. |
| 11,369,421 | B2 | 6/2022 | Harshman et al. |
| 11,419,645 | B2 | 8/2022 | Stinson et al. |
| 11,529,148 | B2 | 12/2022 | Meek et al. |
| 11,826,262 | B2 | 11/2023 | Glerum et al. |
| 11,832,856 | B2 | 12/2023 | Meek et al. |
| 12,023,074 | B2 | 7/2024 | Harshman et al. |
| 12,167,877 | B2 | 12/2024 | Harshman et al. |
| 2002/0032444 | A1 | 3/2002 | Mische |
| 2002/0077631 | A1 | 6/2002 | Lubbers et al. |
| 2002/0087161 | A1 | 7/2002 | Randall et al. |
| 2002/0198527 | A1 | 12/2002 | Muckter |
| 2003/0078582 | A1 | 4/2003 | Heggeness |
| 2003/0181982 | A1 | 9/2003 | Kuslich |
| 2003/0187449 | A1 | 10/2003 | McCleary et al. |
| 2003/0229351 | A1 | 12/2003 | Tidwell et al. |
| 2004/0011565 | A1 | 1/2004 | Lyon et al. |
| 2004/0024409 | A1 | 2/2004 | Sand et al. |
| 2004/0050568 | A1 | 3/2004 | Orozco |
| 2004/0102778 | A1 | 5/2004 | Huebner et al. |
| 2004/0215191 | A1 | 10/2004 | Kitchen |
| 2005/0055023 | A1 | 3/2005 | Sohngen et al. |
| 2005/0082824 | A1 | 4/2005 | Luettgen et al. |
| 2005/0085819 | A1 | 4/2005 | Ellis et al. |
| 2005/0154390 | A1 | 7/2005 | Matthis et al. |
| 2005/0165401 | A1 | 7/2005 | Pack |
| 2006/0074421 | A1 | 4/2006 | Bickley et al. |
| 2006/0264950 | A1 | 11/2006 | Nelson et al. |
| 2007/0083204 | A1 | 4/2007 | Sidebotham |
| 2007/0162132 | A1 | 7/2007 | Messerli |
| 2007/0173834 | A1 | 7/2007 | Thakkar |
| 2007/0208364 | A1 | 9/2007 | Smith et al. |
| 2007/0233111 | A1 | 10/2007 | Orbay et al. |
| 2008/0051786 | A1 | 2/2008 | Jensen |
| 2008/0058722 | A1 | 3/2008 | Von et al. |
| 2008/0077133 | A1 | 3/2008 | Schulze |
| 2008/0077154 | A1 | 3/2008 | Edwards et al. |
| 2008/0108989 | A1 | 5/2008 | Parsell et al. |
| 2008/0161805 | A1 | 7/2008 | Saravia et al. |
| 2008/0181740 | A1 | 7/2008 | Waitszies |
| 2008/0195145 | A1 | 8/2008 | Bonutti et al. |
| 2008/0234676 | A1 | 9/2008 | Schulze et al. |
| 2008/0249628 | A1 | 10/2008 | Altarac et al. |
| 2008/0269745 | A1 | 10/2008 | Justin |
| 2008/0287951 | A1 | 11/2008 | Stoneburner et al. |
| 2008/0294163 | A1 | 11/2008 | Chou et al. |
| 2008/0294164 | A1 | 11/2008 | Frank et al. |
| 2008/0319455 | A1 | 12/2008 | Harris et al. |
| 2009/0024174 | A1 | 1/2009 | Stark |
| 2009/0048672 | A1 | 2/2009 | Essenmacher |
| 2009/0062797 | A1 | 3/2009 | Huebner et al. |
| 2009/0149710 | A1 | 6/2009 | Stefanchik et al. |
| 2009/0192512 | A1 | 7/2009 | Sommers |
| 2009/0216232 | A1 | 8/2009 | Buford et al. |
| 2009/0228008 | A1 | 9/2009 | Justin et al. |
| 2009/0299343 | A1 | 12/2009 | Rogers |
| 2010/0023010 | A1 | 1/2010 | Nelson et al. |
| 2010/0076503 | A1 | 3/2010 | Beyar et al. |
| 2010/0185290 | A1 | 7/2010 | Compton et al. |
| 2010/0217333 | A1 | 8/2010 | McShane et al. |
| 2010/0249832 | A1 | 9/2010 | Thomas et al. |
| 2010/0249838 | A1 | 9/2010 | Stopek et al. |
| 2010/0249854 | A1 | 9/2010 | Thomas et al. |
| 2010/0249944 | A1 | 9/2010 | Thomas et al. |
| 2010/0262239 | A1 | 10/2010 | Boyden et al. |
| 2010/0286692 | A1 | 11/2010 | Greenhalgh et al. |
| 2010/0298893 | A1 | 11/2010 | Stucki |
| 2010/0318137 | A1 | 12/2010 | Stucki et al. |
| 2010/0331842 | A1 | 12/2010 | Milbank |
| 2011/0015684 | A1 | 1/2011 | Belcheva et al. |
| 2011/0028974 | A1 | 2/2011 | Chemello |
| 2011/0040282 | A1 | 2/2011 | Uihlein |
| 2011/0046746 | A1 | 2/2011 | Rabiner et al. |
| 2011/0087227 | A1 | 4/2011 | Mazur et al. |
| 2011/0098757 | A1 | 4/2011 | Schelling |
| 2011/0098816 | A1 | 4/2011 | Jacob et al. |
| 2011/0098817 | A1 | 4/2011 | Eckhardt et al. |
| 2011/0119815 | A1 | 5/2011 | Paulson et al. |
| 2011/0144643 | A1 | 6/2011 | Lorenz et al. |
| 2011/0144645 | A1 | 6/2011 | Saravia et al. |
| 2011/0144703 | A1 | 6/2011 | Krause et al. |
| 2011/0153454 | A1 | 6/2011 | Dunn et al. |
| 2011/0184518 | A1 | 7/2011 | Trieu |
| 2011/0184519 | A1 | 7/2011 | Trieu |
| 2011/0184520 | A1 | 7/2011 | Trieu |
| 2011/0196435 | A1 | 8/2011 | Forsell |
| 2011/0218644 | A1 | 9/2011 | Meridew et al. |
| 2011/0230966 | A1 | 9/2011 | Trieu |
| 2011/0238181 | A1 | 9/2011 | Trieu |
| 2011/0264229 | A1 | 10/2011 | Donner |
| 2011/0288598 | A1 | 11/2011 | Moed et al. |
| 2011/0306975 | A1 | 12/2011 | Kaikkonen et al. |
| 2011/0319944 | A1 | 12/2011 | Borodic |
| 2012/0010617 | A1 | 1/2012 | Ramos |
| 2012/0065638 | A1* | 3/2012 | Moore ............... A61B 17/7225 606/62 |
| 2012/0078252 | A1 | 3/2012 | Huebner et al. |
| 2012/0078311 | A1 | 3/2012 | Huebner et al. |
| 2012/0083847 | A1 | 4/2012 | Huebner et al. |
| 2012/0083895 | A1 | 4/2012 | Conway et al. |
| 2012/0101533 | A1 | 4/2012 | Purcell et al. |
| 2012/0101576 | A1 | 4/2012 | Dewey et al. |
| 2013/0006145 | A1 | 1/2013 | Toomey et al. |
| 2013/0006245 | A1 | 1/2013 | Stoneburner et al. |

(56) References Cited

U.S. PATENT DOCUMENTS

| | | | |
|---|---|---|---|
| 2013/0012942 A1 | 1/2013 | Nelson et al. | |
| 2013/0131678 A1 | 5/2013 | Dahners | |
| 2013/0144348 A1 | 6/2013 | Schwappach | |
| 2013/0325007 A1 | 12/2013 | Beyar et al. | |
| 2014/0114312 A1 | 4/2014 | Krause | |
| 2014/0296853 A1 | 10/2014 | Wolter | |
| 2014/0309636 A1 | 10/2014 | Meek et al. | |
| 2014/0358146 A1 | 12/2014 | Meek et al. | |
| 2015/0012051 A1 | 1/2015 | Warren et al. | |
| 2015/0038970 A1 | 2/2015 | Coope | |
| 2015/0157370 A1 | 6/2015 | Gross | |
| 2015/0257800 A1 | 9/2015 | Harshman et al. | |
| 2015/0297245 A1 | 10/2015 | Lam et al. | |
| 2017/0014170 A1 | 1/2017 | Fallin et al. | |
| 2017/0020585 A1 | 1/2017 | Harshman et al. | |
| 2017/0049460 A1 | 2/2017 | Coope | |
| 2017/0164953 A1 | 6/2017 | Lam et al. | |
| 2017/0238977 A1 | 8/2017 | Harshman et al. | |
| 2018/0092681 A1 | 4/2018 | Lutz | |
| 2018/0296227 A1 | 10/2018 | Meek et al. | |
| 2019/0120282 A1* | 4/2019 | Krause | F16C 1/04 |
| 2019/0231401 A1 | 8/2019 | Harshman et al. | |
| 2019/0282280 A1 | 9/2019 | Harshman et al. | |
| 2020/0038646 A1 | 2/2020 | Sweeney et al. | |
| 2020/0054372 A1* | 2/2020 | Stinson | A61B 17/7208 |
| 2020/0138492 A1 | 5/2020 | Kavanagh | |
| 2021/0220027 A1 | 7/2021 | Harshman et al. | |
| 2021/0322070 A1 | 10/2021 | Koch et al. | |
| 2021/0353338 A1 | 11/2021 | Meek et al. | |
| 2021/0386465 A1* | 12/2021 | Thaler | A61B 17/7208 |
| 2022/0287744 A1 | 9/2022 | Harshman et al. | |
| 2022/0354549 A1 | 11/2022 | Stinson et al. | |
| 2023/0157708 A1 | 5/2023 | Meek et al. | |
| 2023/0248392 A1 | 8/2023 | Whittaker et al. | |
| 2024/0081880 A1 | 3/2024 | Meek et al. | |
| 2024/0307098 A1 | 9/2024 | Harshman et al. | |
| 2025/0064489 A1 | 2/2025 | Harshman et al. | |
| 2025/0325281 A1 | 10/2025 | Meek et al. | |

FOREIGN PATENT DOCUMENTS

| | | | |
|---|---|---|---|
| CA | 2725324 | A1 | 11/2009 |
| CN | 2662839 | Y | 12/2004 |
| CN | 2699846 | Y | 5/2005 |
| CN | 101208053 | A | 6/2008 |
| CN | 101633119 | A | 1/2010 |
| CN | 101636119 | A | 1/2010 |
| CN | 102793579 | A | 11/2012 |
| CN | 103025257 | A | 4/2013 |
| CN | 103200887 | A | 7/2013 |
| CN | 103813764 | A | 5/2014 |
| CN | 104203132 | A | 12/2014 |
| CN | 104837425 | A | 8/2015 |
| CN | 104203132 | B | 8/2017 |
| CN | 107106217 | A | 8/2017 |
| CN | 112955087 | A | 6/2021 |
| EP | 0078619 | A2 | 5/1983 |
| EP | 1941838 | A1 | 7/2008 |
| EP | 2779928 | A1 | 9/2014 |
| EP | 3326558 | A1 | 5/2018 |
| EP | 3206608 | A4 | 7/2018 |
| EP | 3522803 | A1 | 8/2019 |
| EP | 3866712 | A1 | 8/2021 |
| GB | 1494553 | A | 12/1977 |
| WO | 2007009123 | A2 | 1/2007 |
| WO | 2008116175 | A2 | 9/2008 |
| WO | 2008120877 | A1 | 10/2008 |
| WO | 2009143374 | A2 | 11/2009 |
| WO | 2010124230 | A1 | 10/2010 |
| WO | 2011067668 | A1 | 6/2011 |
| WO | 2011119815 | A2 | 9/2011 |
| WO | 2011153454 | A2 | 12/2011 |
| WO | 2012107913 | A2 | 8/2012 |
| WO | 2013063145 | A1 | 5/2013 |
| WO | 2013071432 | A1 | 5/2013 |
| WO | 2014075165 | A1 | 5/2014 |
| WO | 2014075184 | A1 | 5/2014 |
| WO | 2015134750 | A1 | 9/2015 |
| WO | 2016061173 | A1 | 4/2016 |
| WO | 2018067888 | A1 | 4/2018 |
| WO | 2020077457 | A1 | 4/2020 |
| WO | 2020081855 | A1 | 4/2020 |

OTHER PUBLICATIONS

"UT Southwest Medical Surgeons Market Pelvic Fracture Device", Accessed at http://www.texasbusiness.com/ut-southwest-medical-surgeons-market-pelvic-fracture-device-cms-4418, Texas Business.com, Apr. 22, 2011, pp. 1-5.

Barry , et al., "Flexible intramedullary nails for fractures in children", Aspects of Current Management, vol. 86-B, No. 7, British Editorial Society of Bone and Joint Surgery, Sep. 2004, pp. 1-7.

Cheung , et al., "A New Halo-Pelvic Apparatus", Spine, vol. 28, No. 3, pp. 305-308.

Ganz , et al., "Surgical dislocation of the adult hip", The Journal of Bone and Joint Surgery (Br), vol. 83-B, No. 8, British Editorial Society of Bone and Joint Surgery, Nov. 2004, pp. 1119-1124.

Griffin , et al., "Vertically Unstable Pelvic Fractures Fixed with Percutaneous Iliosacral Screws: Does Posterior Injury Jattem Prediction Fixation Failure?", Journal of Orthopedic Trauma, vol. 17, No. 6, Lippincott Williams, and Wilkins, Inc., Jan. 2006, pp. 399-405.

Miller , et al., "Variations in Sacral Morphology and Implications for Iliosacral Screw Fixation", Journal of the American Academy of Orthopaedic Surgeons, vol. 20, No. 1, American Academy of Orthopaedic Surgeons, Jan. 2012, pp. 8-16.

Novick , "Pelvic Fractures/Acetabular Fractures", Hospital for Special Surgery, Mar. 30, 2006, HSS.edu, Mar. 30, 2006, pp. 1-9.

Novick , "Pelvic Fractures/Acetabular Fractures—An Interview with Dr. David L. Helfet", Hospital for Special Surgery, accessed at http://www.hss.edu/conditions-pelvic-acetabulum-fractures.asp, Mar. 30, 2006, 10 Pages.

Starr , "Fractures of the Pelvic Ring", in Rockwood & Green's Fractures in Adults 6th Edition, Chapter-41, accessed on Feb. 4, 2014, Lippincott Williams & Wilkins, pp. 1-40.

Starr , et al., "Superior Pubic Ramus Fractures Fixed With Percutaneous Screws: What Predicts Fixation Failure?", Journal of Orthopaedic Trauma, vol. 22, No. 2, Lippincott Williams and Wilkins, Feb. 2008, pp. 81-87.

Vaidya, R. , et al., "Complications of Anterior Subcutaneous Internal Fixation for Unstable Pelvis Fractures: A Multicenter Study", Clinical Orthopaedics and Related Research, vol. 470, No. 8, Springer, Aug. 2012, pp. 1-8.

* cited by examiner

FIXATION DEVICES AND ASSOCIATED SYSTEMS AND METHODS

CROSS-REFERENCE TO RELATED APPLICATION(S)

The present applications claims the benefit of priority to U.S. Provisional Application No. 63/366,724, filed Jun. 21, 2022, which is incorporated by reference herein in its entirety.

TECHNICAL FIELD

The present technology relates to fixation devices, and in particular to implantable fixation devices.

BACKGROUND

Bone fractures may occur in straight bones, such as the femur, or in curved bones, such as pelvic bones. Repairing a bone fracture generally involves two steps: fracture reduction and fracture fixation. Reduction is the step of reducing the fracture by minimizing the distance between the bone fragments and aligning the bones anatomically to minimize deformity after healing. Both surgical and nonsurgical reduction methods exist. Fixation is the step of holding the bone fracture fragments mechanically stable and in close proximity to each other to promote bone healing which may take several weeks or more, depending on the type of fracture, type of bone and the general health of the patient suffering the injury.

Fixing bone fracture fragments in a mechanically stable manner to eliminate motion across the fracture site also minimizes pain when patients apply weight across the fracture during everyday activities like sitting or walking. Fixation of bone fractures may be accomplished by either internal or external fixation. Internal fixation is defined by mechanically fixing the bone fracture fragments with implanted devices. Examples of internal fixation include bone screws inserted within the bone across the fracture site and bone plates which are applied to the surface of the bone across the fracture site. Bone plates are typically attached to healthy bone using two or more bone screws.

External fixation comprises methods and devices which mechanically fix the bone fracture fragments by application external to the body. The traditional use of a splint or cast are examples of external fixation of a fractured bone. An example of an invasive external fixation device uses long screws that are inserted into bone on each side of the fracture. In pelvic fracture work the use of external skeletal fixation is common and involves placing long threaded pins into the iliac bones and then connecting them with an external frame. These screws are connected to a frame which is located outside the body.

Invasiveness of both fracture reduction and fixation steps varies depending on the devices and/or methods used. Invasive open reduction typically involves surgically dissecting to allow access to the bone fracture. Dissection is performed through the skin, fat, and muscle layers, while avoiding injury to adjacent structures such as nerves, major blood vessels, and organs. Once dissection has been completed, the fracture may be reduced prior to definitive fixation and provisionally held using surgical clamps or other methods. Non-invasive closed reduction is typically performed by applying force to the patient's skin surface at different locations and/or to apply traction to a leg, to reduce the fracture. Minimally invasive reduction techniques minimize the surgical dissection area by reducing the size of the surgical wound and by directly pushing on the bone with various long handled tools through the minimal surgical wound. Invasive open fixation typically involves surgically dissecting to allow access to sufficient areas of healthy bone so that fixation devices such as surgical plates can be attached directly to the bone surface to fix the fracture site. Minimally invasive closed fixation typically involves insertion of a device such as a bone screw or intramedullary rod (or nail) within the bone through a small incision in the skin, fat, and muscle layer.

Minimally invasive reduction and fixation are typically used to repair long bone injuries such as the femur. One example is an intramedullary rod, also known as an intramedullary nail (IM nail), inter-locking nail or Kuntschner nail, all of which are straight devices. Intramedullary nails in the femur and tibia are load sharing devices and can well resist large bending and shearing forces, thereby allowing patients to leave hospital and manage with crutches in a short time.

The mechanical strength of bone fixation is determined by both the strength of the implant and strength of the implant's attachment to healthy bone. The mechanical forces applied across the fracture during the healing process can include shear, compression, tension (tensile), torsion, static loading and dynamic loading. In bones with complex curvature such as bones of the pelvis or of the spine, straight intramedullary fixation devices have limitations. Bone curvature limits the mechanical strength of attaching a straight intramedullary fixation device within healthy bone tissue. In pelvic and acetabular fracture fixation, an example of a straight intramedullary device is a commonly used cannulated bone screw. These screws must be limited in length and diameter because they are a straight device in a curved tunnel. If too long they will penetrate the bone and could injure important soft tissues. Moreover, such screws may not offer secure fixation due to their low tensile pull-out forces in cortical cancellous and/or osteoporotic bone during the healing process. Also, the diameter of the straight intramedullary screw, when in a curved bone, is significantly smaller than the thickness of the cancellous bone layer between the two outer cortical bone layers. Since the cancellous bone is significantly weaker than cortical bone (and can have significantly compromised strength in the case of osteoporotic bone), straight intramedullary screws may allow for the bone fragments to move relative to each other due to inadequate vertical shear holding force of cancellous bone. Plates normally act, mechanically, as tension band plates, neutralization plates or compression plates. Often a single plate will perform more than one of these mechanical functions, but since the plates are attached to the bone, the use of plates requires invasive open surgery to expose the bone. The plates are inherently weak because they are thin and have notches in them so that they can be bent to fit the curves of the pelvis. Invasive open surgery can result in increased blood loss, increased risk of infection and increased healing time compared to minimally invasive methods. Accordingly, there is a need for improved fixation devices.

SUMMARY

The implantable fixation devices of the present technology are configured to address difficult mechanical fixation issues associated with fixation of curved bones, such as found in the pelvic ring and around the acetabulum. The fixation devices of the present technology, for example, can be movable between a curved and straight configuration, and convertible between a flexible and a rigid state. In a flexible state, the fixation device may be inserted within an intramedullary space and conform to a curved pathway. In a rigid state, the fixation device can support the tensile and vertical shear mechanical loads required to fix fractured bone segments.

The subject technology is illustrated, for example, according to various aspects described below, including with reference to FIGS. 1A-18B. Various examples of aspects of the subject technology are described as numbered clauses (1, 2, 3, etc.) for convenience. These are provided as examples and do not limit the subject technology.

1. A fixation device, comprising:
an elongate body comprising a plurality of interconnected segments, each of the segments comprising:
an engagement member,
a recess configured to receive the engagement member of an adjacent one of the segments, and
a plurality of channels, wherein at least one of the channels extends through the engagement member; and
a plurality of flexible elongate members, each extending through one of the channels,
wherein the elongate body is transformable between a flexible configuration in which the elongate members can move relative to one another and a rigid configuration in which the elongate members are fixed relative to one another.

2. A fixation device, comprising:
an elongate body comprising a plurality of interconnected segments, each of the segments comprising:
an engagement member,
a recess configured to receive the engagement member of an adjacent one of the segments, and
a plurality of channels, wherein at least one of the channels is aligned along a circumferential dimension of the corresponding segment with the engagement member of the corresponding segment; and
a plurality of flexible elongate members, each extending through one of the channels,
wherein the elongate body is transformable between a flexible configuration in which the elongate members can move relative to one another and a rigid configuration in which the elongate members are fixed relative to one another.

3. The device of any one of the previous Clauses, wherein the at least one of the channels is fully enclosed by at least a portion of the engagement member.

4. A fixation device, comprising:
an elongate body comprising a plurality of interconnected segments, each of the segments comprising:
an engagement member,
a recess configured to receive the engagement member of an adjacent one of the segments, and
a plurality of channels; and
a plurality of flexible elongate members, each extending through one of the channels, wherein a minimum width of the engagement member is greater than a diameter of the flexible elongate members,
wherein the elongate body is transformable between a flexible configuration in which the elongate members can move relative to one another and a rigid configuration in which the elongate members are fixed relative to one another.

5. The device of any one of the previous Clauses, wherein at least one of the segments includes a plurality of engagement members.

6. The device of any one of the previous Clauses, wherein the engagement member comprises:
a neck extending away from an end face of the segment, and
a broad portion extending away from the neck, wherein the broad portion comprises lateral surfaces and a top surface, and wherein a radius of curvature along the top surface is greater than a radius of curvature along the lateral surfaces.

7. The device of any one of the previous Clauses, wherein the engagement member comprises:
a neck extending away from an end face of the segment, and
a broad portion extending away from the neck, the broad portion having a height to width ratio that is less than one.

8. The device of any one of the previous Clauses, wherein the engagement member comprises:
a neck extending away from an end face of the segment, and
a broad portion extending away from the neck, wherein the broad portion comprises curved lateral sides and a substantially flat top side.

9. The device of any one of the previous Clauses, wherein each of the segments further comprises a lumen extending therethrough, wherein the lumen is configured to receive an elongate guide element.

10. The device of any one of the previous Clauses, wherein the elongate body is configured to be implanted within a patient.

11. The device of any one of the previous Clauses, wherein the elongate body is configured to be implanted in a bone of a patient.

12. The device of any one of the previous Clauses, wherein the elongate body is configured to be implanted within an intramedullary space of a bone of a patient.

13. The device of any one of the previous Clauses, further comprising a distal element disposed at a distal end portion of the elongate body, wherein the distal element is configured to engage a bone.

14. The device of any one of the previous Clauses, further comprising a locking element disposed at a proximal end portion of the elongate body and operably coupled to the elongate members, wherein actuation of the locking element causes the body to transform from the flexible configuration to the rigid configuration.

15. A segment configured for use with a fixation device that comprises a plurality of interconnected segments, the segment comprising:
a body having a first end portion and a second end portion, the body having a recess at the first end portion;
an engagement member extending away from the second end portion of the body, wherein the engagement member is configured to be received within a recess of an adjacent one of the segments, and wherein the engagement member comprises:
a neck having a first end at the second end portion of the body and a second end, and
a broad portion at the second end of the neck, wherein the broad portion comprises lateral sides and a top side, and wherein a radius of curvature of the broad portion along the top side is greater than a radius of curvature along the lateral sides; and a channel extending through the engagement member and the body.

16. A segment configured for use with a fixation device that comprises a plurality of interconnected segments, the segment comprising:

a body having a first end portion and a second end portion, the body having a recess at the first end portion;

an engagement member extending away from the second end portion of the body, wherein the engagement member is configured to be received within a recess of an adjacent one of the segments, and wherein the engagement member comprises:

a neck having a first end at the second end portion of the body and a second end, and a broad portion at the second end of the neck, the broad portion having a height to width ratio that is less than one; and a channel extending through the engagement member and the body.

17. A segment configured for use with a fixation device that comprises a plurality of interconnected segments, the segment comprising:

a body having a first end portion and a second end portion, the body having a recess at the first end portion;

an engagement member extending away from the second end portion of the body, wherein the engagement member is configured to be received within a recess of an adjacent one of the segments, and wherein the engagement member comprises:

a neck having a first end at the second end portion of the body and a second end, and a broad portion at the second end of the neck, wherein the broad portion comprises curved lateral sides and a substantially flat top side; and a channel extending through the engagement member and the body.

18. The segment of any one of Clauses 15-17, wherein the channel is configured to receive an elongate flexible member therethrough.

19. The segment of any one of Clauses 15-18, wherein the engagement member is a first engagement member and the segment further comprises a second engagement member extending away from the second end portion of the body, and wherein the second engagement member is configured to be received within the recess of the adjacent one of the segments.

20. The segment of Clause 19, wherein the channel is a first channel and the segment further comprises a second channel extending through the second engagement member and the body.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

The present technology relates to fixation devices, and in particular to implantable fixation devices. Some embodiments of the present technology, for example, are directed to devices configured to be implanted in an intramedullary space of a bone to fixate one or more fractures in the bone. Specific details of several embodiments of the technology are described below with reference to FIGS. 1A-18B. While the devices, systems, and methods described herein may be used on long and straight bones, the present technology is particularly beneficial for treating curved bones or other body structures. Examples of curved or non-linear bones include the zygoma, mandible (jawbone), clavicle, scapula (the hemipelvis of the upper limb), ribs, spine, talus, calcaneus, and others. The device can also be configured for implantation in pediatric long bones.

In the discussion of the various devices, systems, and methods herein, the term "proximal" refers to the side or end of a device that tends to be the closest to the physician or operator along the longitudinal axis of the device when in use. "Proximal" may also refer to the end or side of the device that is last to enter the patient's body. As used herein, the term "distal" refers to the end or side of the device that is farthest from the physician or operator along the longitudinal axis of the device. "Distal" may also refer to the end or side of the device that is first to enter the patient's body.

Figures 1A, 1B:
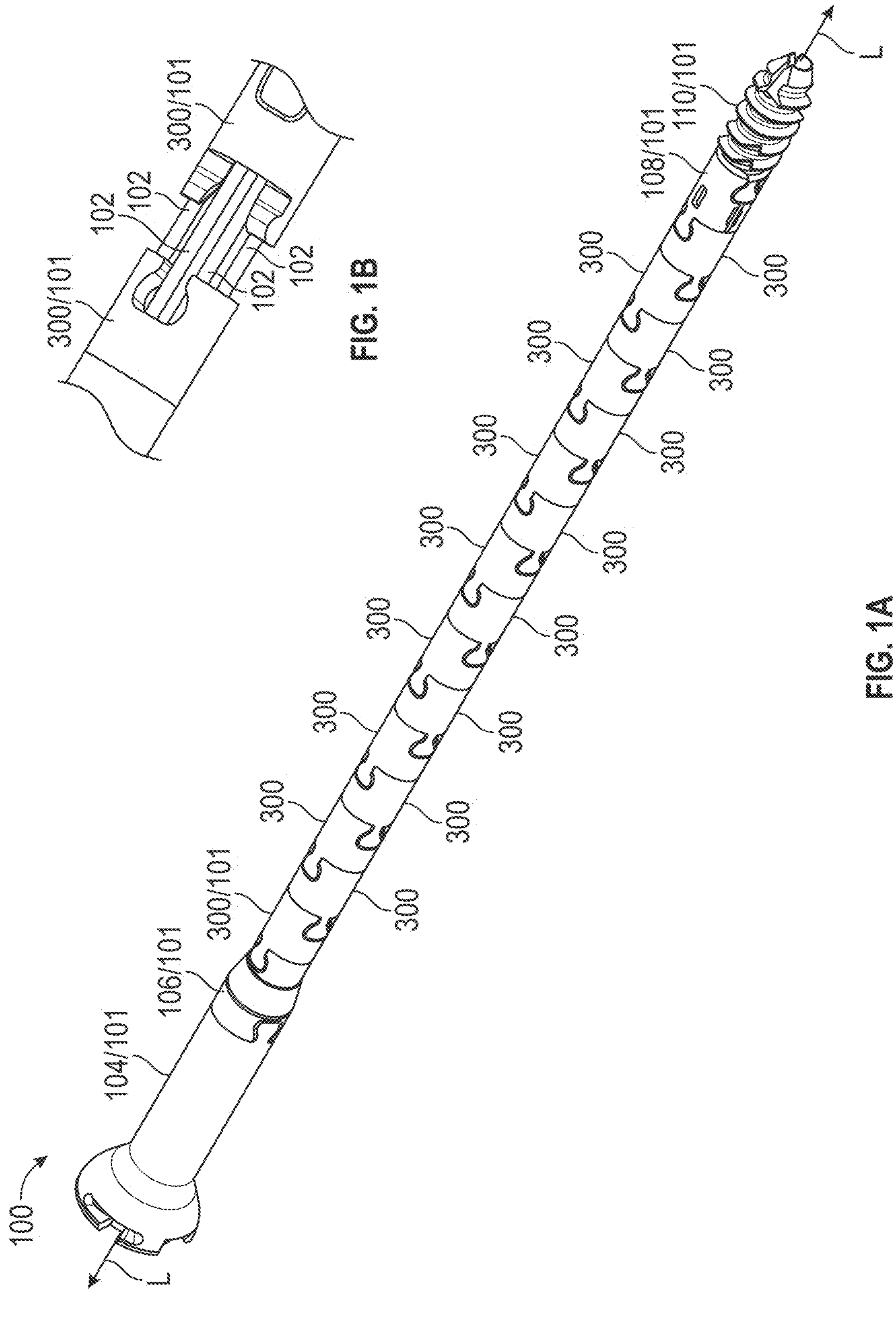
FIG. 1A is a perspective view of a fixation device in a straight configuration, according to several embodiments of the present technology.
FIG. 1B is an enlarged view of the fixation device of FIG. 1A, shown with a segment removed for the purposes of viewing the elongate members, according to several embodiments of the present technology.
Figure 1C:
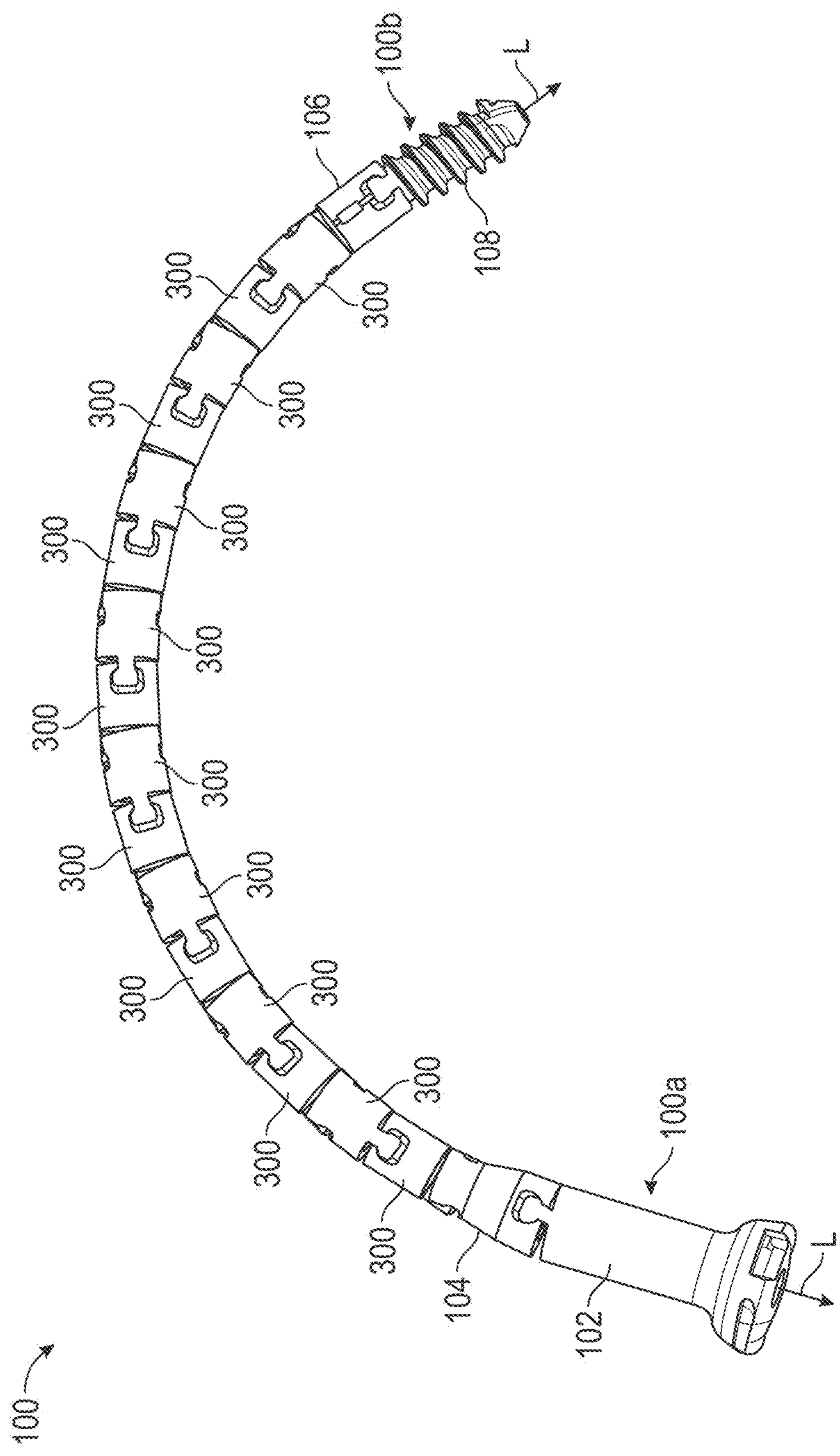
FIG. 1C is a perspective view of the fixation device of FIG. 1A in a curved configuration, according to several embodiments of the present technology.

FIGS. 1A-1C show a fixation device 100 (or "device 100") of the present technology that is configured to be positioned within an intramedullary space of a bone to fixate one or more fractures in the bone. FIG. 1A is a perspective view of the device 100 in a straight configuration, and FIG. 1C shows the device 100 in a curved configuration. Although shown as a single curve in a single plane, the fixation device 100 may be configured to include multiple curves, where one of the curves is in a different plane than at least another one of the curves. FIG. 1B shows an enlarged portion of the device 100 with a segment removed for ease of viewing the elongate members extending through the device 100. Referring to FIGS. 1A-1C, the device 100 can comprise an elongate body formed of a plurality of interconnected segments 101 and a plurality of elongate members 102 (see FIG. 1C) extending longitudinally through the segments 101. The device 100 is transformable between a flexible state and a rigid state. In the flexible state, the elongate members 102 can slide axially and the segments 101 can move and angulate relative to one another, thereby allowing the device 100 to bend and straighten. In the rigid state, the elongate members 102 are fixed relative to one another, thus holding the segments 101 in a desired configuration.

The segments 101 are configured to withstand the torques and other forces that the fixation device 100 may experience during implantation of the fixation device 100, during healing of the fixated fracture(s), and/or during a removal procedure. The segments 101 can comprise the same type of segment or two or more different types of segments. For example, as shown in the device 100 of FIGS. 1A-1C, the fixation device 100 can comprise a plurality of body segments 300 that form the majority of the length of the device 100, a proximal segment 104, and a distal segment 110. The proximal segment 104 is positioned proximal of the body segments 300 along the longitudinal axis of the device 100 and, as described below, can be configured to lock the elongate members 102 relative to one another to rigidize the device 100 in a desired configuration. The distal segment 110 is positioned distal of the body segments 300 along the longitudinal axis of the device 100 and is configured to hold the fixation device 100 in a stable position and orientation while the fixation device 100 is implanted in a bone (such as an intramedullary space of a bone). For example, in some embodiments the distal segment 110 includes relatively sharp threads configured to engage and be screwed into the bone.

Optionally, the device 100 can include one or more transition segments between the body segments 300 and one or both of the proximal and distal segments 104, 110. As shown in FIGS. 1A-1C, for example, the device 100 can include a proximal transition segment 106 between the body segments 300 and the proximal segment 104, and a distal transition segment 108 between the body segments 300 and the distal segment 110. In some embodiments the device 100 does not include one or both of the proximal and distal transition segments 106, 108. Optionally, the device 100 can include one or more spacer segments (not shown) positioned between adjacent body segments and/or between a body segment and the adjacent distal or proximal segment. The lengths of the individual spacer segments can be less than the lengths of the individual body segments 300.

The elongate members 102 can comprise flexible members that extend from a distal portion of the device 100 through at least the body segments 300 to a proximal portion of the device 100. For example, in some embodiments the distal end portions of the elongate members 102 are coupled to the distal segment 110. In some embodiments, the distal end portions of the elongate members 102 are coupled to the distal transition segment 108 (if included in the device 100). Likewise, the proximal end portions of the elongate members 102 can be coupled to the proximal segment 104. In some embodiments, the proximal end portions of the elongate members 102 are coupled to the proximal transition segment 106 (if included in the device 100).

As discussed in greater detail herein, the proximal segment 104 is transformable between an unlocked state in which the elongate members 102 are free to slide relative to one another and a locked state in which the proximal segment 104 prevents the elongate members 102 from sliding relative to one another. In this locked state, the elongate members 102 maintain the fixation device 100 in the shape that the fixation device 100 acquired while it was in its flexible configuration. In some embodiments, for example as shown in FIG. 1A, the fixation device 100 includes four elongate members 102, although the fixation device 100 can include fewer than four elongate members 102 (e.g., one member, two members, three members) or more than four elongate members 102 (e.g., five members, six members, seven members, etc.). Furthermore, each elongate member 102 can be formed from any suitable material, such as a metal or a plastic, and can comprise a single filament or multiple filaments. If multiple filaments, the filaments can be wound about and/or twisted with one another, braided with one another, or other configurations.

According to some embodiments, some or all of the elongate members 102 include retaining elements at their distal end portions to keep the distal ends of the elongate members 102 from slipping through the distal transition segment 108 and/or distal segment 110. For instance, the retaining elements can comprise end caps made from any suitable material, such as steel or another metal. Other retaining element devices are possible. Additionally or alternatively, the proximal ends of the elongate members 102 may also include retaining elements (such as end caps or other devices). In some embodiments, an interior region of the proximal or distal segment (and/or transition segment) has one or more retaining features configured to engage a portion of a respective elongate member 102 to prevent the elongate member 102 from sliding out of the segment.

The fixation device 100 can include a guidewire channel (not visible in FIGS. 1A-1C) extending along the longitudinal axis L of the fixation device 100. The channel can extend from the proximal segment 104 through the body segments 300 and into the distal segment 110. In some embodiments the channel can terminate distally within the distal transition segment 108. The guidewire channel can be configured to receive a guidewire such that during an implantation procedure, a surgeon can slide the fixation device 100 over a guidewire that was previously inserted into an intramedullary space of a fractured bone. Typically, after the fixation device 100 is implanted, the surgeon removes the guidewire through the guidewire channel.

Figure 2:
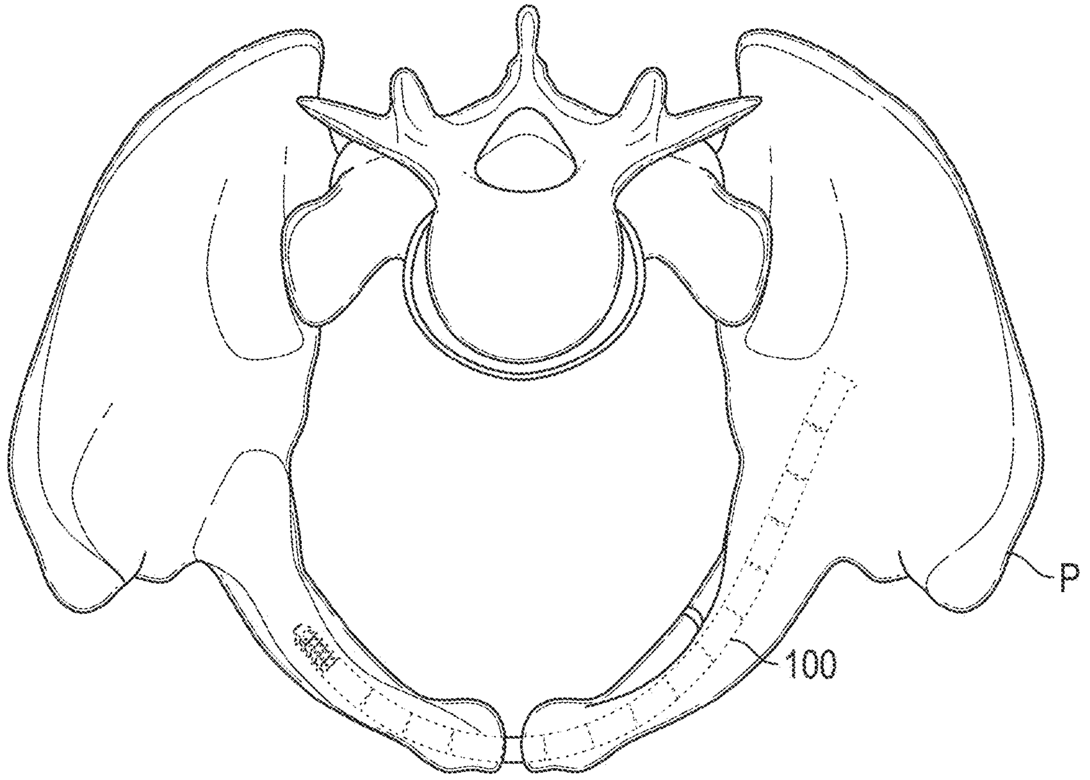
FIG. 2 shows the fixation device of FIGS. 1A-1C implanted in a fractured pelvic bone.

An example placement of the device 100 across a fracture in a pelvic bone is shown in FIG. 2. According to several methods of use, a small hole can be drilled through the cortex of a fractured bone and a guidewire can be introduced into the medullary space of the bone. The guidewire is then advanced under visual guidance, for example by drilling or hammering (depending on the type of fracture and location). A flexible reamer can be placed over the guidewire and drilled over the guidewire to make a tunnel in the bone. Depending on the location and nature of the fracture to be treated, one or more guidewire exchanges may be performed. The reamer can be removed and the device 100 is then screwed into the tunnel over the guidewire. Once in place, the device 100 is made rigid by activating the proximal segment 110 (as detailed below).

Figure 3A:
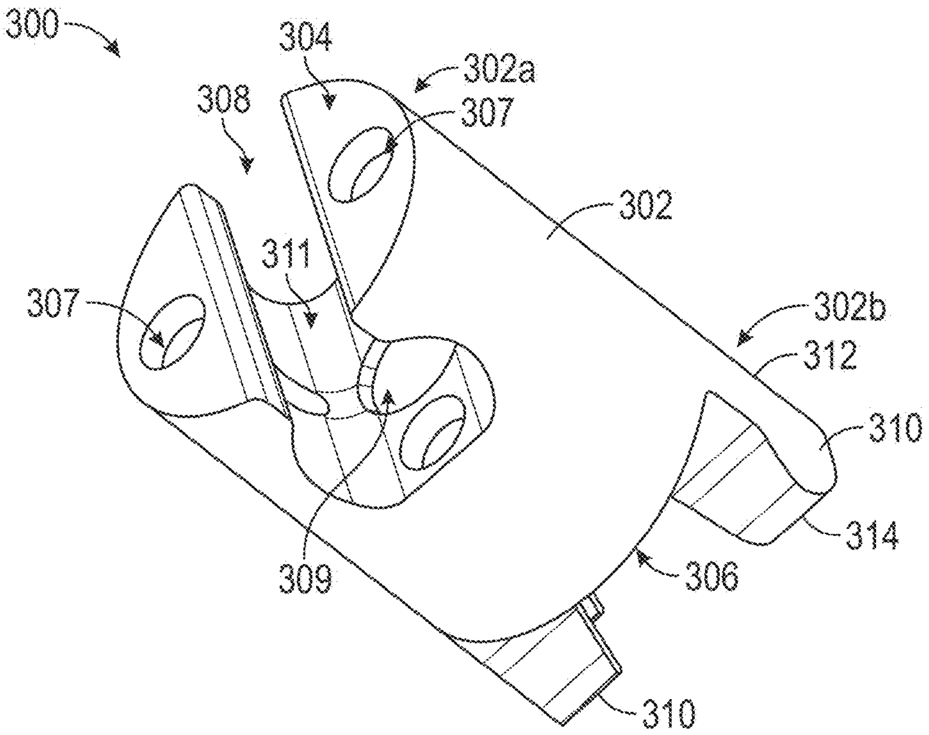
FIGS. 3A and 3B are different perspective views of an isolated segment of a fixation device according to several embodiments of the present technology.
Figure 3B:
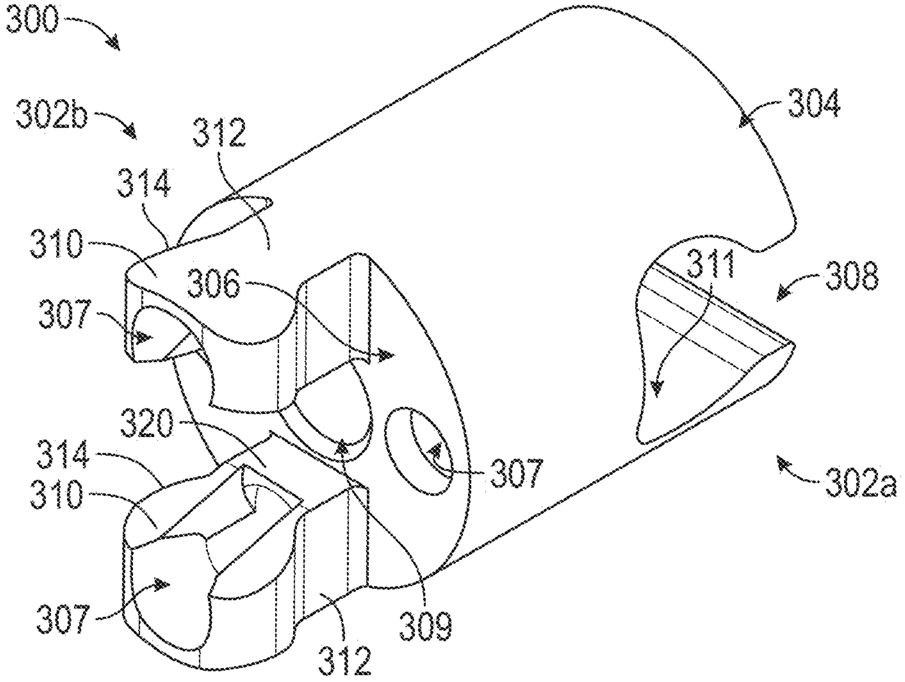
Figure 3C:
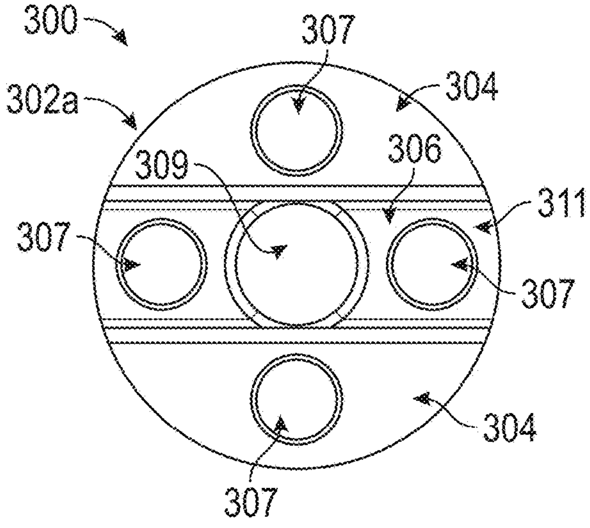
FIGS. 3C and 3D are different end views of the segment of FIGS. 3A and 3B, in accordance with several embodiments of the present technology.
Figure 3D:
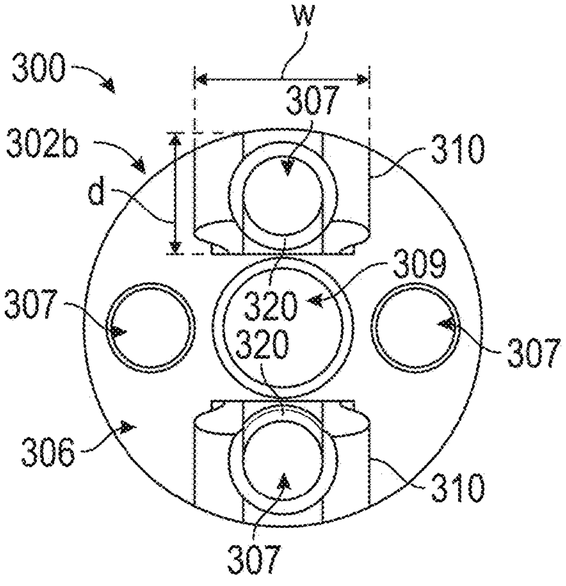
Figure 3E:
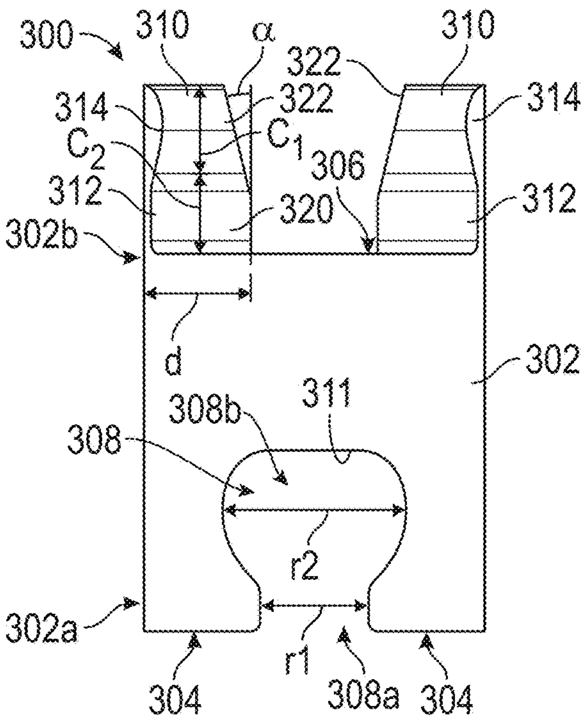
FIGS. 3E and 3F are different side views of the segment of FIGS. 3A and 3B, in accordance with several embodiments of the present technology.
Figure 3F:
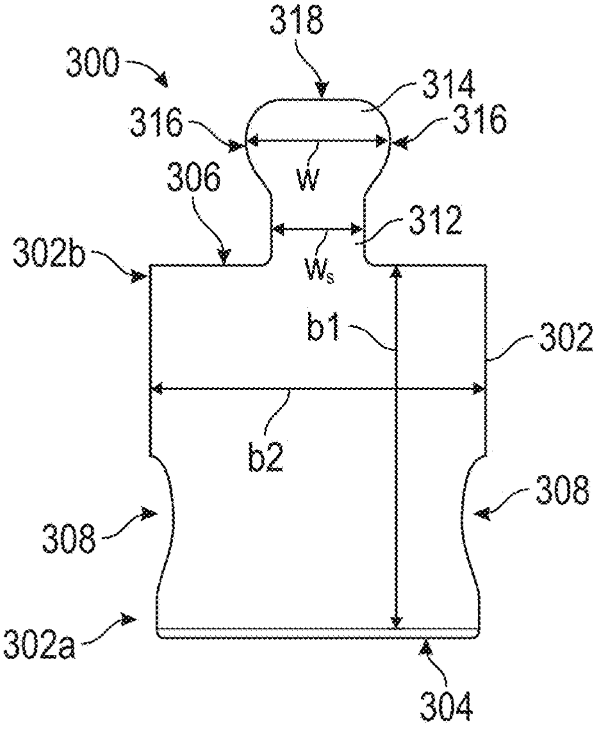

FIGS. 3A-3F show different views of a body segment 300 (or "segment 300") configured in accordance with several embodiments of the present technology. The segment 300 can have a base 302 and a plurality of engagement members 310 extending away from the base 302. The base 302 can have first and second end portions **302*a* and 302*b*, a length b1 (FIG. 3F) measured between the end portions 302*a* and 302*b*, and a cross-sectional dimension b2 (FIG. 3F). The engagement members 310 can be disposed at the second end portion 302*b* of the base 302, and the base 302 includes a recess 306 at the first end portion 302*a* that is configured to receive an engagement member 310 of an adjacent segment of the device 100. The segment 300 further comprises a plurality of channels 307, each configured to receive an elongate member 102 therethrough. The segment 300 can optionally comprise a guidewire channel 309 configured to receive a guidewire therethrough. As shown in FIGS. 3A-3F, at least one of the channels 307 can extend through one of the engagement members 310**.

In some embodiments, the base 302 is substantially cylindrical and has a first end face 304 at the first end portion **302*a* and a second end face 306 at the second end portion 302*b*. The first end face 304 can be split into two portions, one on either side of the recess 308. The engagement members 310 can be continuous with and extend away from the second end face 306. In some embodiments, each of the first and second end faces 304, 306 are substantially flat (e.g., lying in a plane that is substantially perpendicular to a longitudinal axis of the segment 300). In certain embodiments, one or both of the first and second end faces 304, 306 lie in a plane that is disposed at a non-90-degree angle to the longitudinal axis. At least some of the inlet and outlet openings of the channels 307 can be disposed on the first end face 304, the second end face 306, the surface 311 defining the recess 308 at the first end portion 302*a*, and the engagement members 310. As shown in FIGS. 3A-3F, one or more of the channels 307 can extend between a first opening at the second end face 302*b* and an opening in the surface 311 defining the recess 308. It will be appreciated that the base 302** can have other suitable shapes and configurations.

Each engagement member 310 can comprise a stem 312 and a head 314 having a greater width w (FIGS. 3D and 3F) than a width $w_s$ of the stem 312. The stem 312 can have a first end at the second end portion **302*b* of the base 302 and a second end, and the head 314 can be disposed at the second end of the stem 312. Referring to FIG. 3F, the head 314 can comprise lateral sides 316 and a top side 318. The lateral sides 316 can be curved (as shown in FIG. 3F) or may be linear (not shown). Likewise, the top side 318 can be curved (not shown) or linear (as shown in FIG. 3F). In any case, a radius of curvature of the head 314 along the top side 318 can be greater than a radius of curvature of the head 314 along the lateral sides 316. As a result, the head 314 can have a height to width ratio of less than one. In some embodiments, for example as shown in FIGS. 3A-3F, the lateral sides 316 can be curved while the top side 318 is substantially flat. The curved sides 316 allow rotation and other movement of the segment 300 relative to the other segments with reduced or no interference with the elongate members 102 that extend through the channels 307. The shape of the head 314 can be advantageous as it configures the engagement members for engagement with the surface 311 defining the recess 308 to transmit a relatively large torque while allowing full movement of the fixation device 100 in all directions to obtain, during an insertion procedure, any curvature within the capability of the fixation device 100. Moreover, the flattened top side of the head 314 (at least relative to the lateral sides) reduces interference with the elongate members 102 and guidewire as they pass between the abutting ends of adjacent segments, especially when the device 100** is in a curved configuration and the segments/channels are not perfectly aligned.

Referring again to FIGS. 3A-3F, each of the engagement members 310 can have one of the channels 307 extending therethrough. For example, such channels 307 can extend between an opening at the top side 318 of the respective engagement member 310, through the head 314 and stem 312, and through the length of the base 302 until terminating at an opening at the first end face 304. The engagement members 310 can have a width w (FIG. 3D) and a depth d (FIG. 3D) that can both spatially accommodate and structurally support a channel 307 (and the elongate member 102 extending therethrough) as well as withstand the torsional loads exerted on the engagement members 310 during an insertion procedure.

In some embodiments, the engagement members 310 do not fully surround the channel 307. For example, as best shown in FIGS. 3B and 3D, a sidewall of the engagement member 310 surrounds less than a full circumference of the channel 307 along the head 314 such that there exists a gap in the sidewall at an inner side of the engagement member 310. The portion of the sidewall at the head 314 can surround at least 50% of the circumference of the channel 307. In some embodiments the sidewall at the head 314 surrounds 100% of the channel 307. Additionally or alternatively, the sidewall can extend fully around the channel 307 along the stem 312 of the engagement member 310 (e.g., at inner sidewall portion 320). In other embodiments, the sidewall surrounds less than a full circumference of the channel 307 along the stem 312 such that there exists a gap in the sidewall at an inner side of the engagement member 310. In such embodiments, however, the torsional strength of the engagement member 310 may be reduced. The inclusion of an inner sidewall along at least a portion of the engagement member 310 (such as sidewall portion 320) can be advantageous to support the strength of the stem 312, as an open rail extending along the entire length of the engagement member 310 could be prone to collapse or pinching the elongate members 102 at lower torques in the stem 312.

In some embodiments, at least one of the engagement members 310 does not have a channel 307 extending therethrough.

Referring now to FIG. 3E, in some embodiments the engagement members 310 have a chamfered inner surface 322. The chamfered surface 322 can begin at a height c1 above the second end face 306 (e.g., the height of the stem 312), extend for a perpendicular height c2 (e.g., the height of the head 314), and make an angle α with respect to the height dimension of the engagement member 310. In some embodiments, c1 can be from about 0.3 mm to about 2.3 mm, and may be, for example, about 1.6 mm. In certain embodiments, c2 can be about 1.0 mm to about 3.0 mm, and may be, for example, about 1.7 mm. In some embodiments, a can be from about 5° to about 20°, and may be, for example, about 15°. The chamfered surface 322 facilitates bending of the fixation device 100 (FIGS. 1A-1C) while a guidewire is present within the guidewire channel 309.

The engagement members 310 are configured to provide a torque transfer of from about 2 Newton-meters (Nm) to about 20 Nm along the length of the fixation device 100 despite being contoured to prevent interference with the elongate members 102 and guidewire that pass through the segments. In some embodiments, the engagement members 310 are configured to provide a torque transfer of greater than 10 Nm along the length of the fixation device 100. The curved lateral sides 316 enable rotation of the segments 300 with respect to neighboring segments 300 (or transition segments, spacer segments, a distal segment, or a proximal segment) to obtain a minimum radius of curvature for the fixation device 100, which, in some embodiments, is in a range of about 50 mm to about 80 mm, and may be, for example, about 60 mm, or about 65 mm, without interfering with the elongate members 102. Furthermore, the chamfered surface 322 of the engagement members 310 can be at an angle that enables passage of the guidewire at a desired maximum radius of curvature of the fixation device 100. In some embodiments, the engagement members 310 can have a height (c1+c2 in FIG. 3E) and a depth d (FIGS. 3D and 3E) that enable a relatively high torque transfer and a relatively high engagement of the segments 101 to prevent separation of the segments 101 while the fixation device 100 is being torqued, and to enable a tight radius of curvature while still allowing passage of the guidewire.

In some embodiments, the height b1 of the base 302 may be in a range of approximately, 6.5 mm-8.5 mm, and may be, for example, approximately 7.5 mm, and the diameter b2 may be in a range of approximately 4.0 mm-24.0 mm (e.g., about 5 mm or less, about 6 mm or less, about 7 mm or less, about 8 mm or less, about 9 mm or less, about 10 mm or less, etc.).

Different combinations and numbers of segments can be utilized to create different-length devices from, e.g., 50 millimeters (mm) to 250 mm long. Longer or shorter devices can also be created for bone fixation in longer or shorter intramedullary bone pathways. In some embodiments, the fixation device 100 is available in lengths that are in increments of 10 mm (e.g., 50 mm, 60 mm, 70 mm, 80 mm, 90 mm, 100 mm, 110 mm, 120 mm, 130 mm, 140 mm, 150 mm, 160 mm, 170 mm, 180 mm, etc.).

The recess 308 can have a shape complementary to that of the engagement member 310 and may extend across the entire cross-sectional dimension b2 (FIG. 3F) of the base 302. In some embodiments the recess 308 extends less than the entire cross-sectional dimension of the base b2 and/or the base 302 comprises multiple separate recesses. The recess 308 is configured to receive the engagement members 310 of another segment in a manner that allows the two segments to rotate relative to one another so that the fixation device 100 can bend and curve. The width of the recess 308 can be slightly larger than the width of the stem 312 of the engagement member 310 to allow movement of one segment 300 relative to another segment, but not too large to allow the engagement members 310 and the recess 308 to become disconnected during rotation (torque and transmission), bending, and other movements of the fixation device 100. The recess 308 may comprise a first portion 308*a* and a second portion 308*b* having a width r2 greater than a width r1 of the first portion 308*a*.

As best shown in the end views of FIGS. 3C and 3D, the channels 307 can be evenly spaced (e.g., approximately 900 apart) around a periphery of the base 302, and the guidewire channel 309 can be centered on the base 302. In some embodiments, the channels 307 do not have even spacing and/or the guidewire channel 309 can be non-centrally positioned. The openings to the channels 307 can be chamfered to reduce and/or eliminate wear on the elongate member 102 extending through the channel 307 and on the sides of the channel 307 itself as compared to an elongate member 102 and channel 307 of similar sizes with no chamfering. Although the fixation device 100 and segments 300 shown in FIG. 1A comprise four channels, the fixation device 100 and segments 300 can comprise more or fewer channels (e.g., one channel, two channels, three channels, five channels, six channels, etc.). In some embodiments, the channels 307 have a diameter of from about 1.2 mm to about 1.8 mm, and each elongate member 102 has a diameter of from about 1.0 mm to about 1.6 mm.

The guidewire channel 309 can have an outer diameter which is, in some embodiments, in a range of from about 1.0 mm to about 3.0 mm, and which may be, for example, about 2.0 mm, and has a chamfer with an angle which is, in some embodiments, in a range of from about 0° to about 60°, and which may be, for example, about 45°. The guidewire channel 309 can have a chamfer that reduces and/or eliminates wear on the guidewire and on the sides of the guidewire channel 309 itself as compared to a guidewire and guidewire channel of similar sizes with no chamfering.

Figure 4:
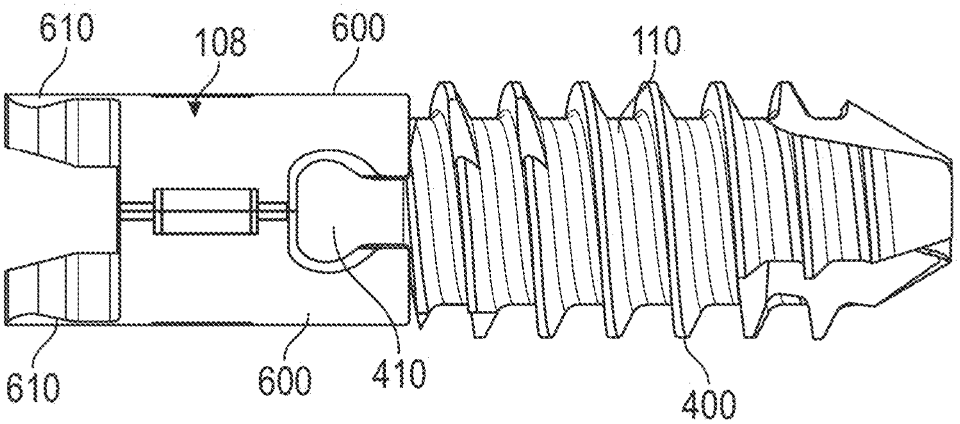
FIG. 4 is a side view of a distal portion of a fixation device configured in accordance with several embodiments of the present technology.
Figure 5:
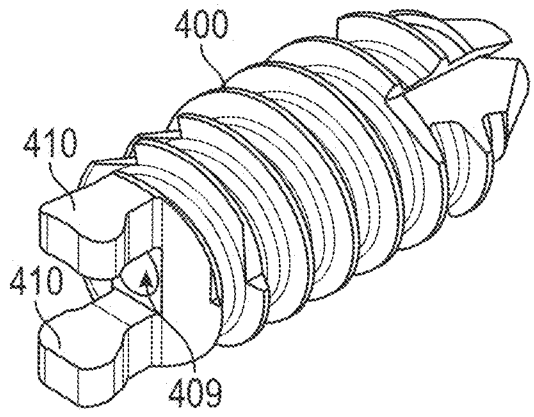
FIG. 5 is a perspective view of a distal segment configured in accordance with several embodiments of the present technology.
Figure 6:
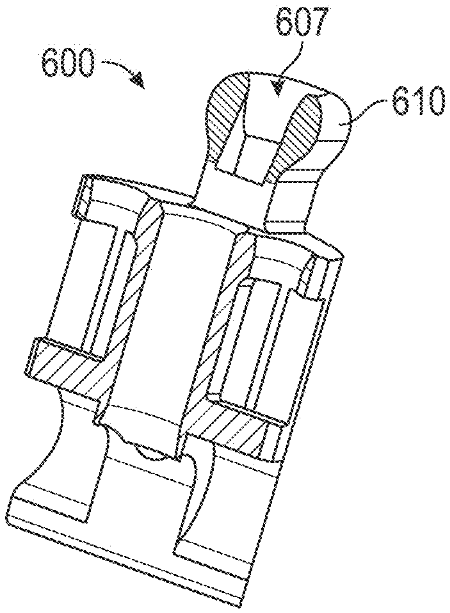
FIG. 6 is a perspective view of a portion of a distal transition segment configured in accordance with several embodiments of the present technology.

FIG. 4 is a side view of a distal portion of a fixation device configured in accordance with several embodiments of the present technology. FIG. 5 is a perspective view of the distal segment 110 of the distal portion, and FIG. 6 is a perspective view of a portion of the distal transition segment 108. In some embodiments the distal portion only comprises the distal segment 110 and does not include a distal transition segment 108. Referring to FIGS. 4-6 together, the distal segment 110 can comprise an engagement portion 400 and a plurality of engagement members 410 extending proximally from the engagement portion 400 and configured to engage a complementary recess on the distal transition segment 108 or an adjacent body segment 300. Unlike the engagement members 310 of the body segments 300, the engagement members 410 of the distal segment 110 do not have channels extending therethrough. In other embodiments, however, one or more engagement members 410 of the distal segment 110 can have a channel extending therethrough. In certain embodiments the distal segment 110 does not include any engagement members and instead is configured to receive an engagement member of an adjacent segment.

In some embodiments, the engagement portion 400 of the distal segment 110 can be a screw thread. The screw thread may have cutting edges for cutting both when the distal segment 110 is rotated either clockwise or counterclockwise. In some embodiments the engagement portion 400 can be one or more of a frangible screw, spikes, pins, clips, grommets, claws, bumps, wires, washers or similar features that are able to provide mechanical engagement between the distal end of the fixation device and the bone. The engagement portion 400 can optionally include a guidewire channel 409 configured to receive a distal end of a guidewire.

According to several embodiments of the present technology, including as shown in FIGS. 4-6, the distal transition segment 108 can comprise two discrete portions 600 that are configured to come together to form a full segment that interlocks with the distal segment 110. Each of the portions 600 can include an engagement member 610 with features that are similar to the engagement members 310 of the body segments 300 disclosed herein. For example, the engagement member 610 can have a shape as described above with reference to engagement members 310 and can have a channel 607 extending therethrough that is configured to receive one of the elongate members 102.

In some embodiments, the elongate members 102 terminate within the distal transition segment 108. For example, the distal transition segment 108 and/or distal ends of the elongate members 102 can comprise one or more retaining elements configured to fix the distal ends of the elongate members 102 in place within the distal transition segment 108, or at least prevent the distal ends of the elongate members 102 from sliding proximally and disengaging the distal transition segment 108. In some embodiments, the elongate members 102 are fixed within the distal segment 110.

Figure 7A:
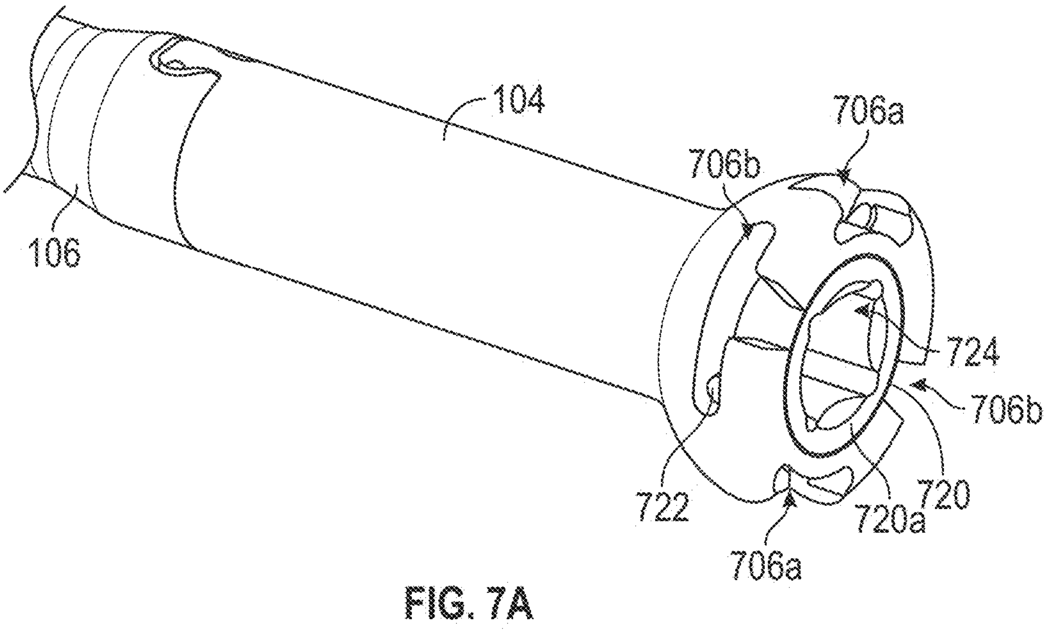
FIG. 7A is a side view of a proximal portion of a fixation device in an unlocked state and configured in accordance with several embodiments of the present technology.
Figure 7B:
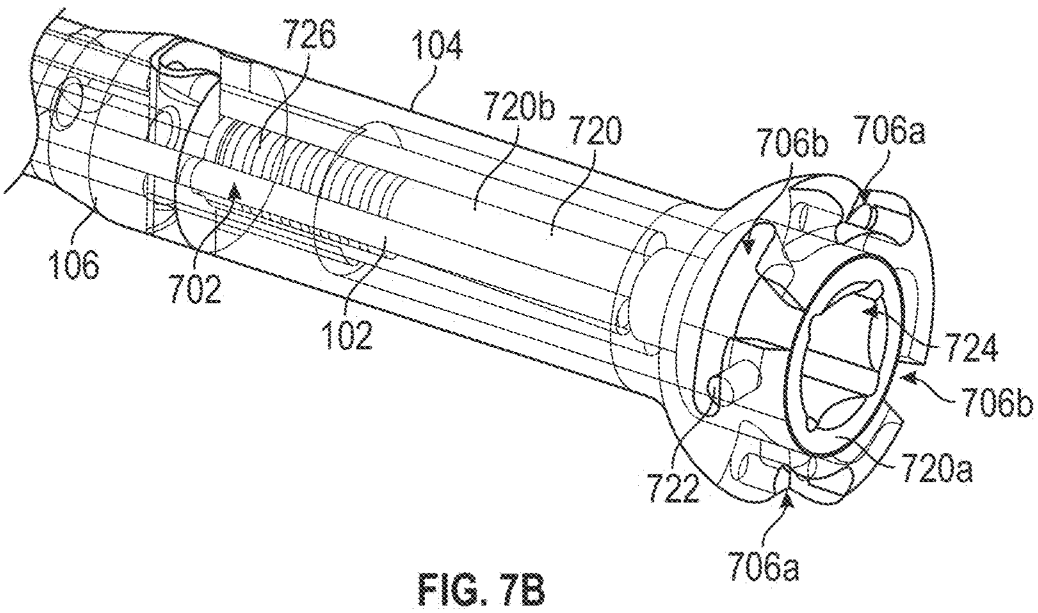
FIG. 7B is a transparent perspective view of the proximal segment shown in FIG. 7A.

FIGS. 7A and 7B are a side views of a proximal portion of a fixation device configured in accordance with several embodiments of the present technology. As shown, in some embodiments the proximal portion of the device comprises a proximal segment 104 and a proximal transition segment 106. The proximal segment 104 can be configured to be manipulated by one or more tools to lock and unlock the fixation device in a desired configuration. In FIGS. 7A and 7B, the proximal segment 104 is shown in an unlocked configuration. In some embodiments, the proximal segment 104 can comprise a sidewall that defines a plurality of internal channels 702 (see transparent view of FIG. 7B), each configured to receive a proximal end of one of the elongate members 102. Each of the elongate members 102 may comprise a respective cap at or near its proximal-most end, which can be compression fitted onto the end of the elongate member 102 and which can be similar to the previously mentioned caps. The elongate members 102 and/or proximal segment 104 can likewise have other retaining members, as described herein. The sidewall can also have a plurality of slots 706 (also referred to herein as first and second slots **706*a* and 706*b*). The first slots 706*a* can be configured to receive a portion of a tool (such as tang 804 of tool 800), and the second slots 706*b* can be configured to receive a pin 722 of a lock 720 (described below) positioned within the proximal segment 104**.

In some embodiments the fixation device further includes a lock 720 positioned partially or completely within a lumen of the sidewall of the proximal segment 104. The lock 720 can comprise a proximal head **720*a* and a distal extension 720*b*. The proximal head 720*a* can have an opening 724 configured to receive a tool for rotating the lock 720 and one or more pins 722 extending away from the head 720*a*. When the lock 720 and proximal segment 104 are assembled, the pins 722 are received within the second slots 706*b* of the proximal segment 104. The distal extension 720*b* of the lock 720 can comprise a cam 726 (see transparent view of FIG. 7B). Rotation of the lock 720 relative to the proximal segment 104 causes the pins 722 to slide within the second slots 706*a* and activates the cam 726**, as detailed below.

Figure 8:
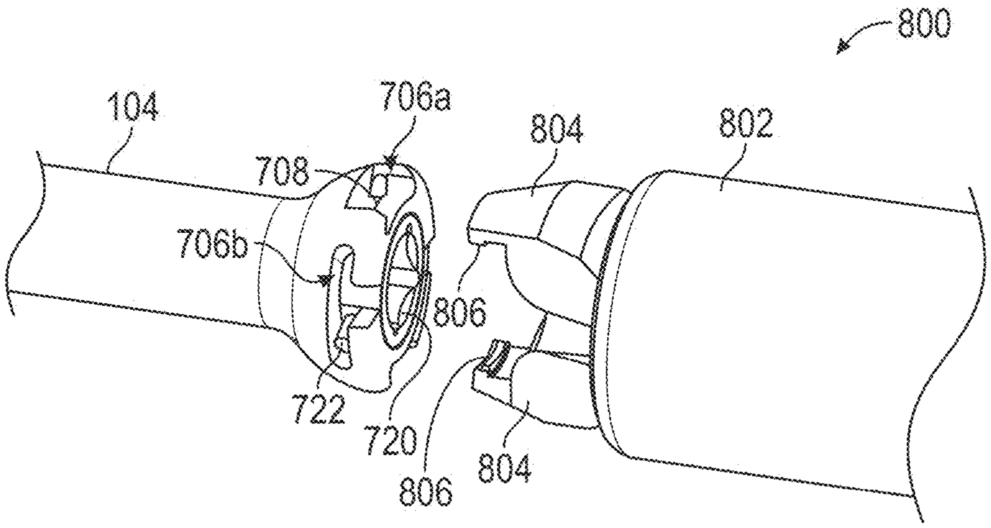
FIG. 8 shows a tool in the process of engaging a proximal segment of a fixation device configured in accordance with several embodiments of the present technology.

FIG. 8 shows a tool 800 in the process of engaging the proximal segment 104. The tool 800 can be configured to engage the proximal segment 104 to insert the fixation device into a bone or to extract (remove) the fixation device from the bone (extraction is optional). In some embodiments, for example as shown in FIG. 8, the tool 800 comprises a sheath 802 and an elongated body extending through the sheath 802 with one or more tangs 804 at its distal end. The tool 800 is configured to secure the fixation device while allowing the lock 720 to rotate (via another tool advanced through a lumen of tool 800) in order to lock the fixation device into a rigid configuration (whether straight or curved) or unlock the fixation device into a flexible configuration. In either case, the tangs 804 of the tool 800 can be placed into the first slots **706*a* of the proximal segment 104 and the sheath 802 can be advanced at least partially over the tangs 804 to press the tangs 804 inward. Ridges 806 on the ends of the tangs 804 engage a shelf 708 within the first slots 706*a* of the proximal segment 104. When pressed inward enough, the tangs 804 can be locked into the first slots 706*a*, thereby securing the tool 800** to the fixation device.

Figure 9:
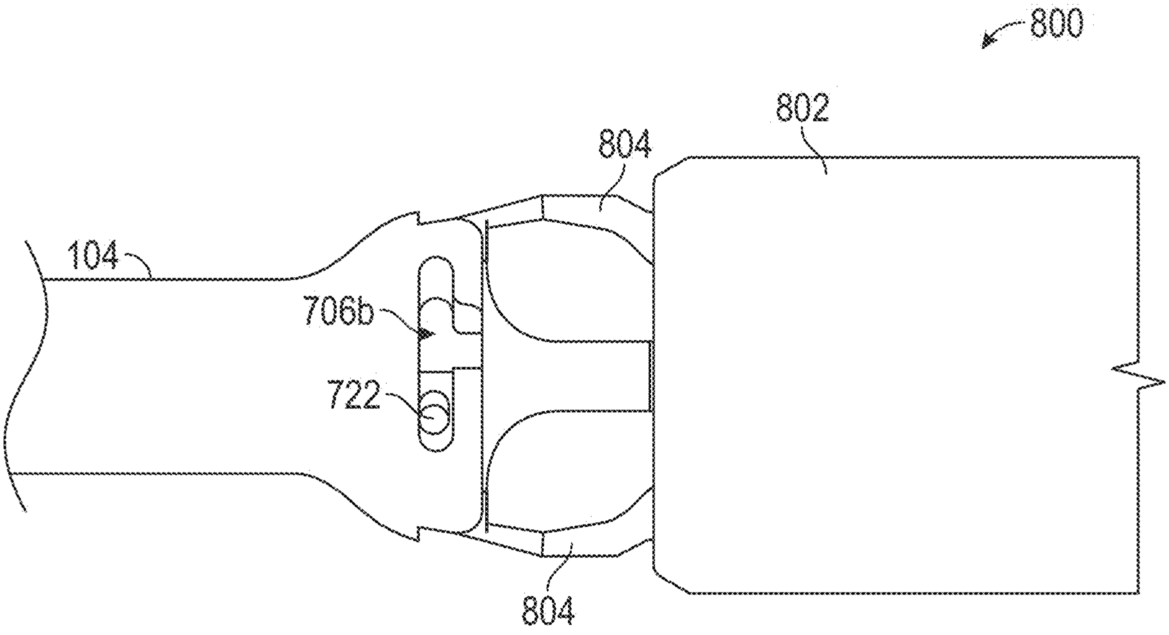
FIG. 9 shows a tool engaging a proximal segment of a fixation device of the present technology while the proximal segment is in an unlocked state.

FIG. 9 shows the tool 800 engaging the proximal segment 104 in an unlocked state with the pin(s) 722 in a first position within the second slot(s) **706*b*. When the fixation device is in an unlocked state, the elongate members 102 are not fixed securely at the proximal portion of the fixation device. For example, when the fixation device is in the unlocked state, the cam 726 can be oriented such that the elongate members 102 are free to slide within the channels 702 (see FIG. 7**B) and, therefore, are free to slide relative to one another axially in response to a bending of the fixation device. The fixation device is typically in the unlocked state while a surgeon is screwing, or otherwise urging, the fixation device into and through the intramedullary space of a fractured bone during an implantation procedure, or while the surgeon is screwing, or otherwise pulling, the fixation device out from the intramedullary space during an extraction procedure.

Figure 10A:
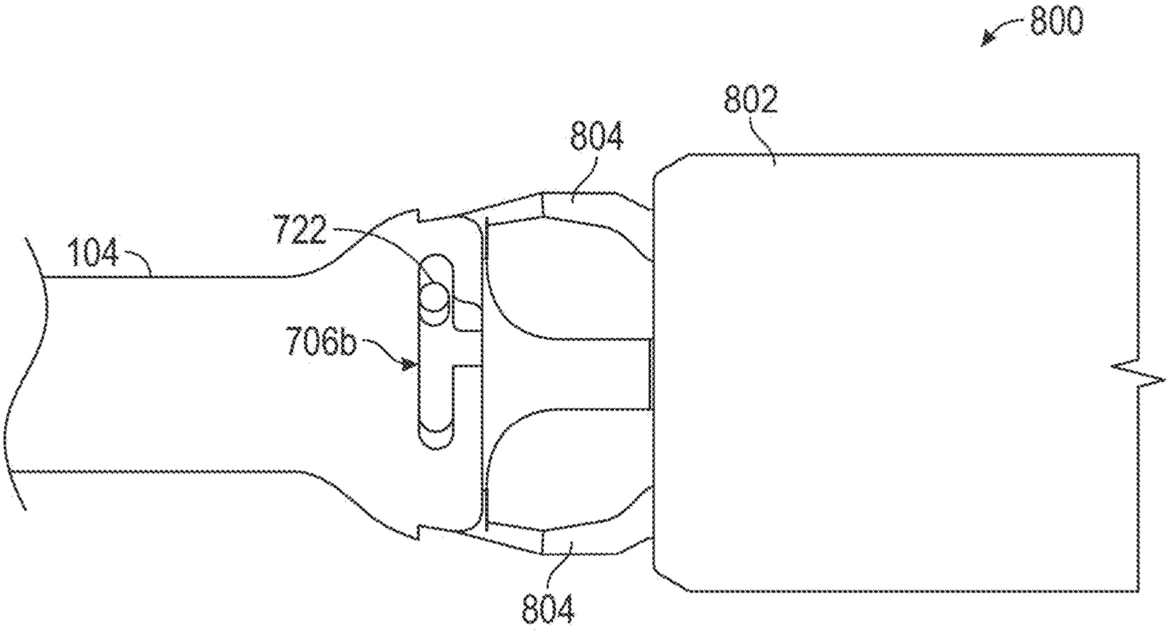
FIG. 10A shows a tool engaging a proximal segment of a fixation device of the present technology while the proximal segment is in a locked state.
Figure 10B:
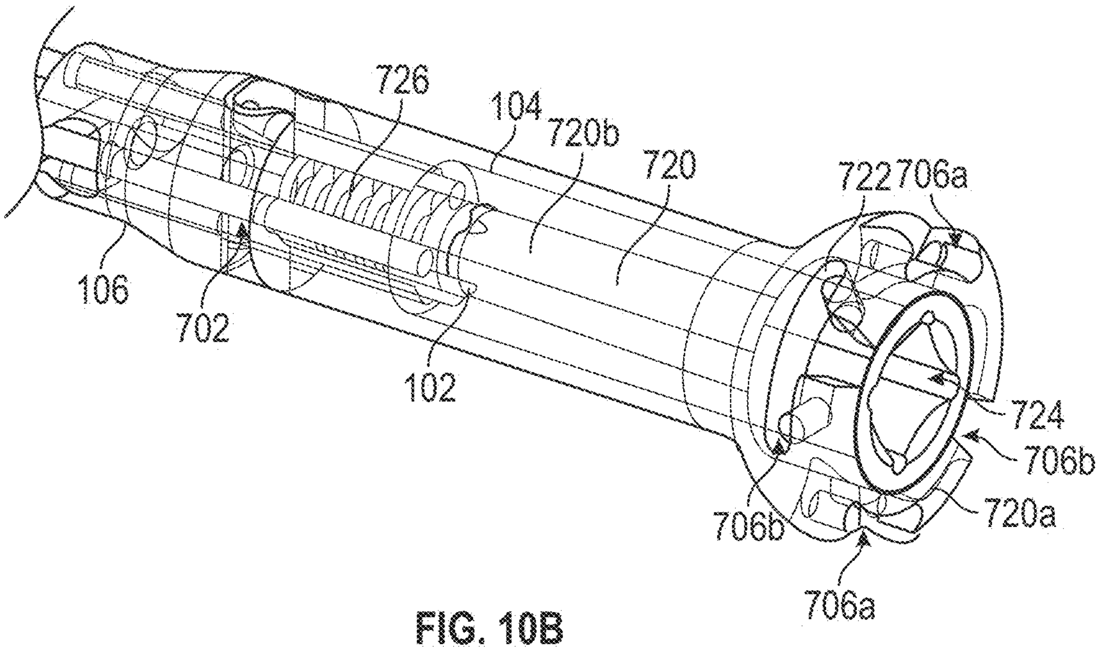
FIG. 10B is a transparent perspective view of a proximal segment of a fixation device of the present technology in a locked state.

FIG. 10A shows a tool 800 engaging a proximal segment 104 in a locked state, and FIG. 10B is a transparent perspective view of the proximal segment 104 in a locked state. In FIGS. 10A and 10B, the pin(s) 722 is in a second position in the second slot(s) **706*b*. To transition the fixation device from an unlocked configuration (as shown in FIGS. 7A, 7B, and 9) to a locked configuration, an operator can insert a tool into the opening 724 of the lock 720 (while the proximal segment 104 is held in place by another tool, such as tool 800) and rotate the cam 726 (clockwise or counterclockwise) until the cam 726 engages the elongate members 102 and compresses them against the inner wall of the sidewall of the proximal segment 104. While the fixation device is locked, the positions of the elongate members 102 relative to one another are fixed such that the elongate members 102** are unable to slide past one another in an axial dimension, thus rigidizing the device.

To transition the fixation device from a locked configuration to an unlocked configuration (or rigid to flexible configuration), an operator can insert a tool into the opening 724 of the lock 720 (while the proximal segment 104 is held in place by another tool, such as tool 800) and rotate the cam 726 (counterclockwise or clockwise, whichever is opposite of the locking direction) until the cam 726 disengages and releases the elongate members 102 such that the elongate members 102 are no longer compressed against the inner wall(s) of the housing of the proximal segment 104. As previously mentioned, while the fixation device is in a curved configuration, at least one of the elongate members 102 has a slightly different bend radius than at least one other of the elongate members 102, and elongate members 102 with different bend radii each have a slightly different linear length between two arbitrary points along the body of the fixation device. Thus, while the proximal ends of the elongate members 102 are shown in FIG. 10B as fairly aligned, in many cases the ends of the elongate members 102 will be staggered, as different elongate members 102 will be extending different lengths depending on the curvature of the fixation device. Regardless, the proximal ends of the elongate members 102 terminate do not extent as far proximally in the locked state shown in FIG. 10B versus the unlocked state of FIG. 7B.

FIGS. 11-18B show different segment designs, all for use with the fixation devices of the present technology. Any of the features of the segments shown in FIGS. 11-18B can be mixed and matched, including with the features of the segments shown and described in FIGS. 1A-10B. In the description below, like numerals identify elements similar to those described above.

Figure 11:
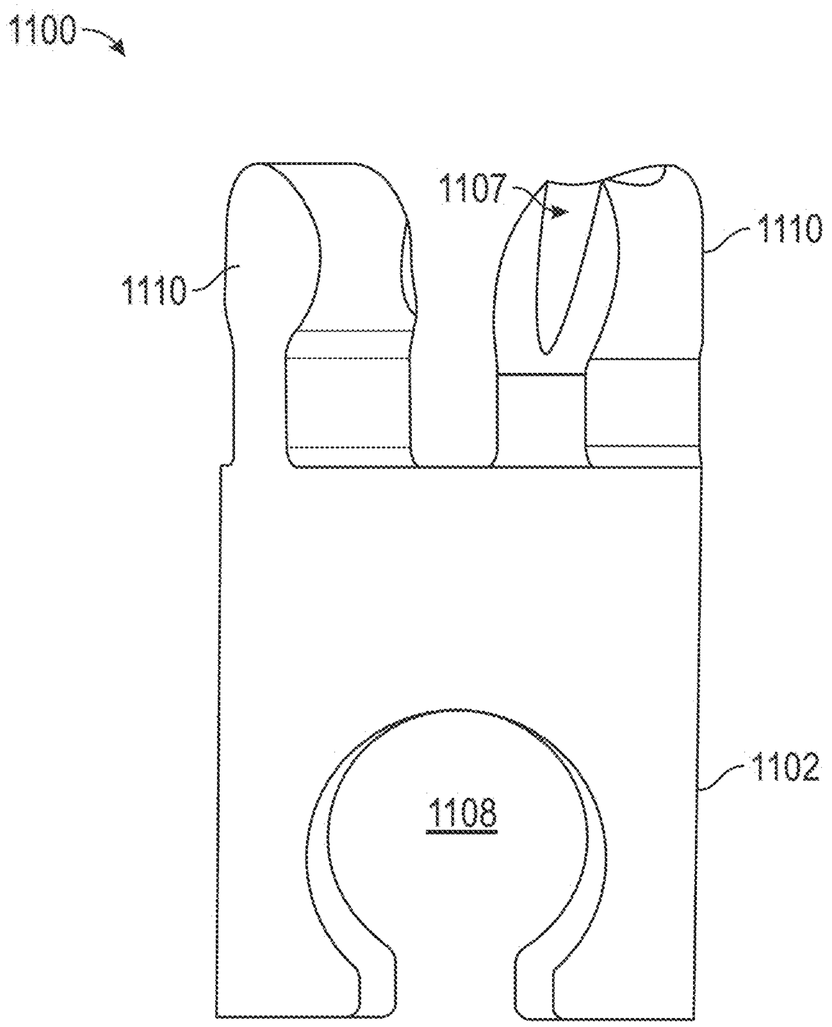
FIG. 11 shows a segment configured for use with the fixation devices of the present technology.

FIG. 11 shows a segment 1100 configured for use with the fixation devices of the present technology. As shown in FIG. 11, in some embodiments the engagement members 1110 of the segment 1100 can have channels 1107 that are substantially v-shaped. In the particular embodiments shown in FIG. 11, the segment 1100 comprises three channels 1107. In other embodiments, the segment 1100 of FIG. 11 can have more or fewer channels 1107, such as two channels, four channels, etc.

Figure 12:
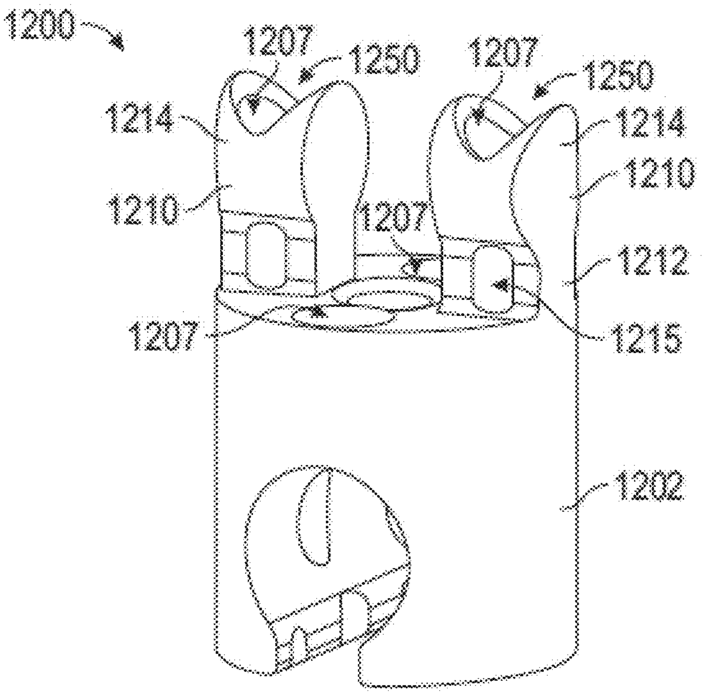
FIG. 12 shows a segment configured for use with the fixation devices of the present technology.

FIG. 12 shows a segment 1200 configured for use with the fixation devices of the present technology. As shown in FIG. 12, in some embodiments the engagement members 1210 can have an inner sidewall such that the engagement member 1210 fully surrounds the channel 1207. A top side of the engagement member 1210 can have a wedge-shaped opening leading into the channel 1207. Additionally or alternatively, the engagement member 12010 can have a stem 1212 with openings 1215 extending across a width of the respective stem.

Figure 13:
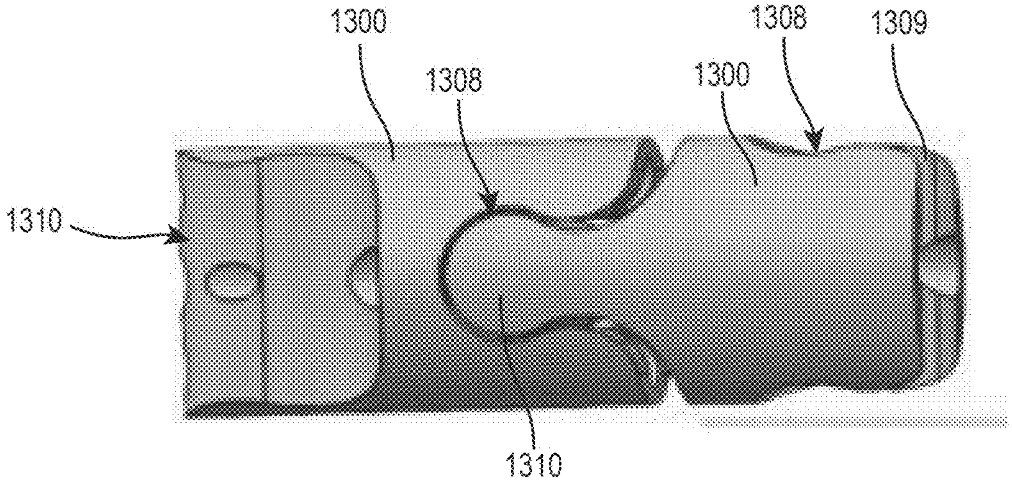
FIG. 13 shows a segment assembled with another segment in accordance with several embodiments of the present technology.

FIG. 13 depicts a segment 1300 configured for use with the fixation devices of the present technology, shown assembled with another segment 1300. As shown in FIG. 13, the segment 1300 can have a single, continuous engagement member 1310 that spans a width of the segment 1300. The bottom surface 1309 of the segment 1300 can be curved, thereby allowing rotation in a single plane. While the segment 1300 has limited motion relative to several of the other embodiments disclosed herein, the continuous engagement member 1308 enables greater torque transmission.

Figure 14:
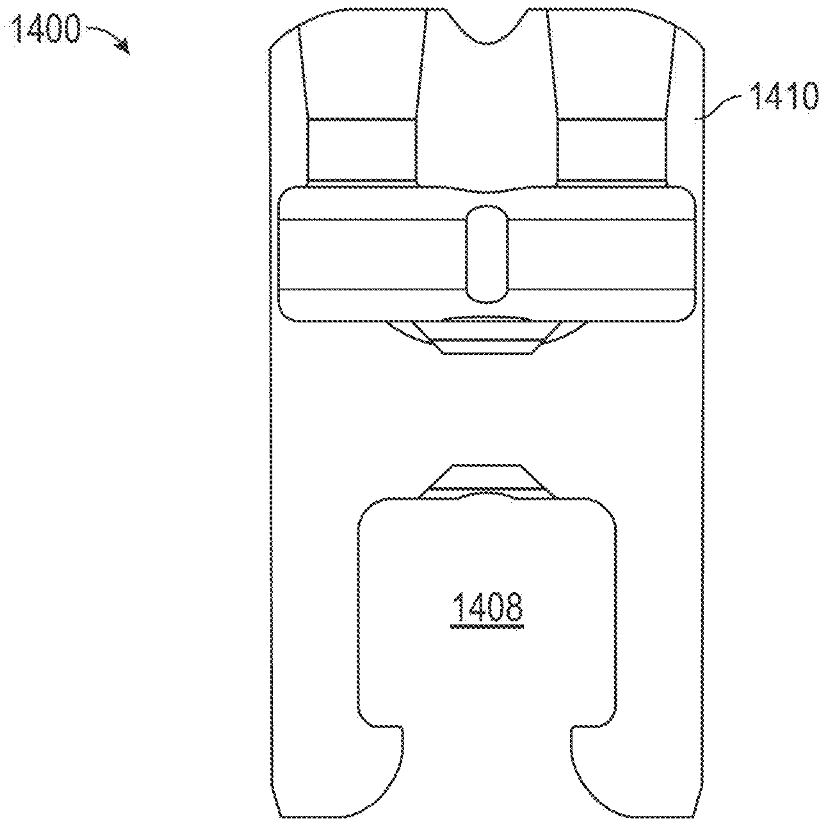
FIG. 14 shows a segment configured for use with the fixation devices of the present technology.
Figure 15:
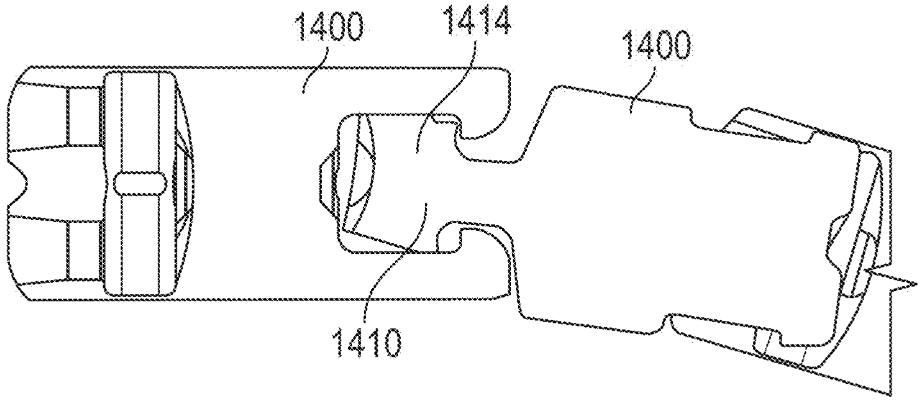
FIG. 15 shows the segment of FIG. 14 assembled with another segment in accordance with several embodiments of the present technology.

FIG. 14 shows a segment 1400 configured for use with the fixation devices of the present technology. FIG. 15 shows the segment of FIG. 14 assembled with another segment in accordance with several embodiments of the present technology. As shown in FIG. 14, the segment 1400 can comprise a square-shaped engagement member 1410 and have a complementary recess 1408. In contrast to the segment 300, the head 1614 of the engagement member 1410 has substantially linear lateral sides.

Figure 16:
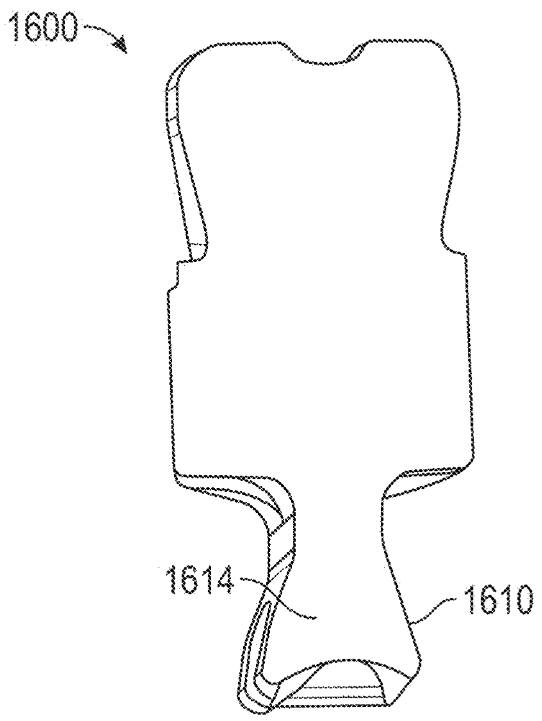
FIG. 16 shows a segment configured for use with the fixation devices of the present technology.
Figure 17:
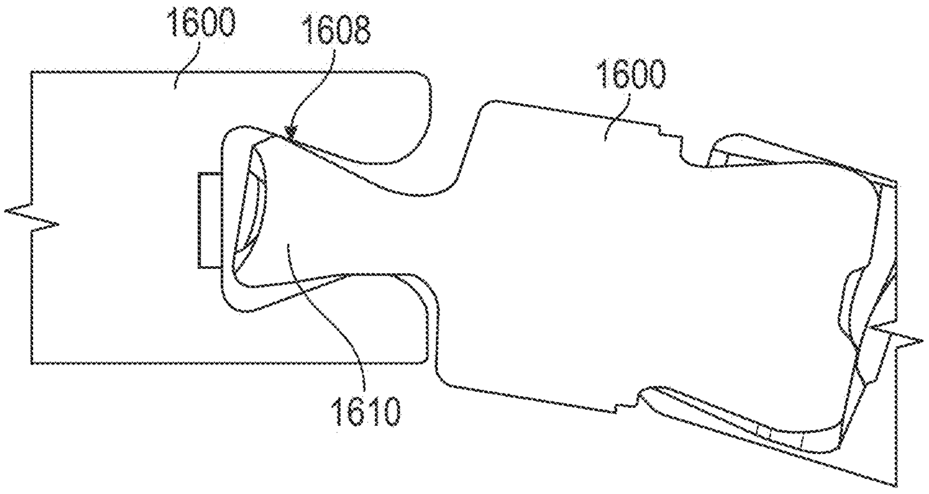
FIG. 17 shows the segment of FIG. 16 assembled with another segment in accordance with several embodiments of the present technology.

FIG. 16 shows a segment 1600 configured for use with the fixation devices of the present technology. FIG. 17 shows the segment of FIG. 16 assembled with another segment in accordance with several embodiments of the present technology. As shown in FIG. 16, the segment 1600 can comprise a triangular engagement member 1610 and have a complementary recess 1608. In contrast to the segment 300, the head 1614 of the engagement member 1610 has substantially linear, angled lateral sides.

Figure 18A:
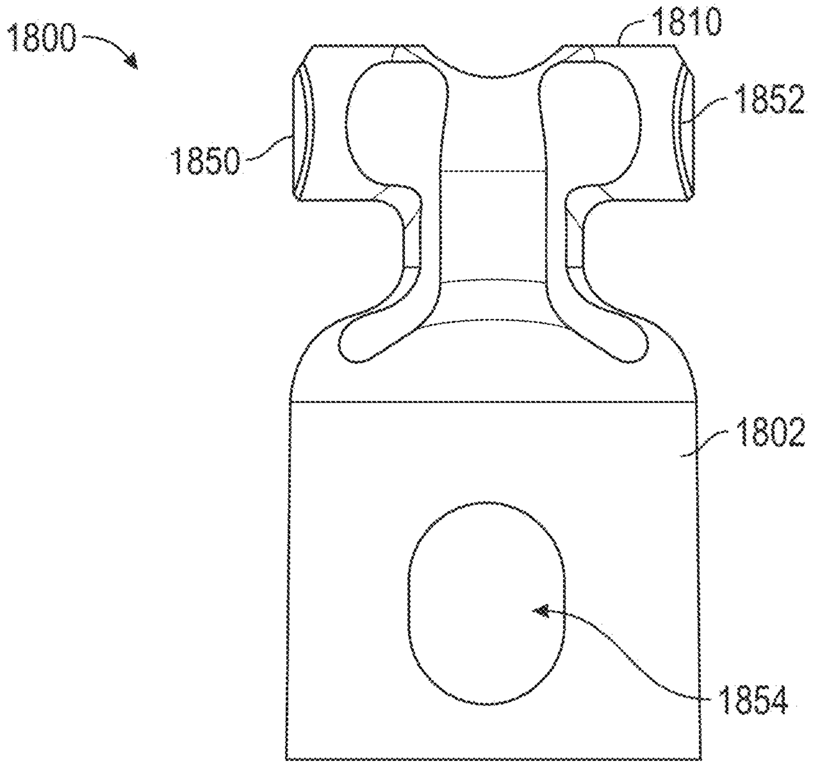
FIGS. 18A and 18B are different views of a segment configured for use with the fixation devices of the present technology.
Figure 18B:
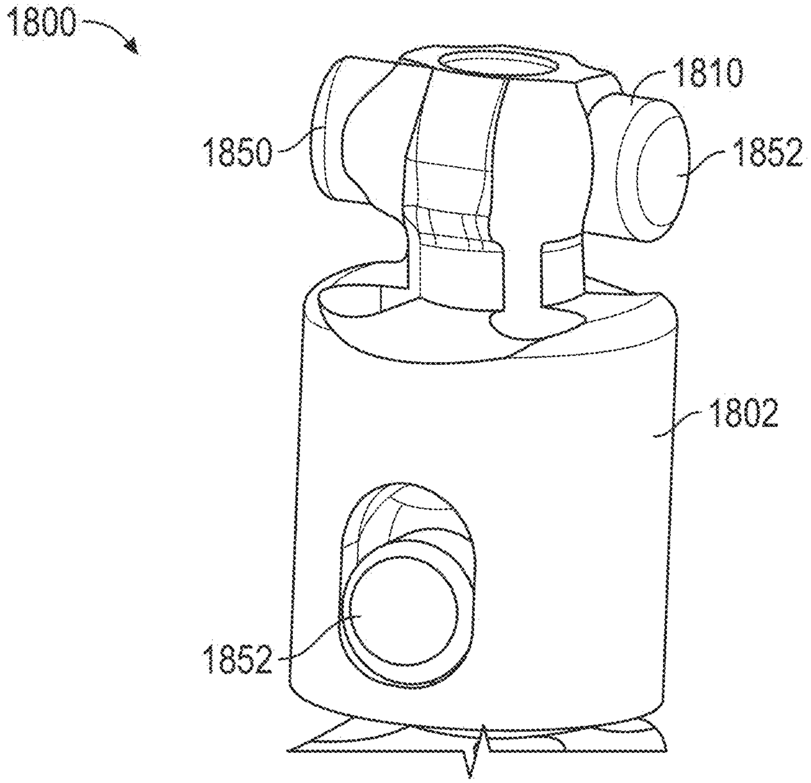

FIGS. 18A and 18B are different views of a segment 1800 configured for use with the fixation devices of the present technology. As shown, the segment 1800 can comprise a single engagement member 1810 that branches laterally into a first engagement arm 1850 and a second engagement arm 1852, each of which is configured to be received within a lateral opening 1854 in a base 1802 of an adjacent segment.

In the various embodiments described herein, the fixation device may be composed from a polymer, a metal, an alloy, or a combination thereof, which may be biocompatible. For example, any of the fixation devices can be formed from titanium or a titanium alloy. Other suitable metals may include stainless steel, cobalt-chromium alloys, and tantalum. In some embodiments, metal alloys having shape memory capability, such as nickel titanium or spring stainless steel alloys, may also be used. In some embodiments, the fracture stabilization device can be formed from a suitable polymer including non-degradable polymers, such as polyetheretherketone (PEEK) and polyethylene (PE), as well as modified versions of these materials (for example, PEEK+calcium phosphates and PE+vitamin E, metal coatings, or surface texturing). Additional non limiting polymers may include; polyether-block co-polyamide polymers, copolyester elastomers, thermoset polymers, polyolefins (e.g., polypropylene or polyethylene, including high density polyethylene (HDPEs), low-density polyethylene (LDPEs), and ultrahigh molecular weight polyethylene (UHMWPE)), polytetrafluoroethylene, ethylene vinyl acetate, polyamides, polyimides, polyurethanes, polyvinyl chloride (PVC), fluoropolymers (e.g., fluorinated ethylene propylene, perfluoroalkoxy (PEA) polymer, polyvinylidenefluoride, etc.), polyetheretherketones (PEEKs), PEEK-carbon fiber composites, Polyetherketoneketones (PEKKs), poly(methylmethacrylate) (PMMA), poly sulfone (PSU), epoxy resins and silicones. Additionally starch based polymers may be used.

Additional materials may include carbon and polyaramid structures, glass or fiberglass derivatives, ceramic materials, and artificial biocompatible protein derivatives (recombinant derived collagen). In other embodiments, the fixation devices of the present technology may be made of a metal and/or alloy segments with a polymer shell, or a sandwich style and coaxial extrusion composition of any number of layers of any of the materials listed herein. Various layers may be bonded to each other to provide for single layer composition of metal(s), alloys, and/or polymers. In another embodiment, a polymer core may be used with a metal and/or metal alloy shell, such as a wire or ribbon braid.

Additionally, at least a portion of the fixation devices of the present technology may include a bone integration surface to promote bone ingrowth, on-growth, and/or through-growth between the segments, if desired. The bone integration surfaces can comprise a three-dimensional space to allow bone integration into and/or onto portions of the fixation device. The three-dimensional space can be provided by a three-dimensional substrate, for example segments, and/or by the provision of holes through the bone integration portions. Other methods for achieving bone integration can include the provision of an appropriate surface topography, for example a roughened or textured area and/or by the provision of osteoconductive coatings, such as calcium phosphates. The bone integration surface may enable the fracture stabilization device to provide a metal and/or polymeric scaffold for tissue integration to be achieved through the fracture stabilization device. In various embodiments, various materials may be used to facilitate, stimulate, or activate bone growth. A non-limiting list of materials may include hydroxyapatite (HA) coatings, synthetic bioabsorbable polymers such as poly (α-hydroxy esters), poly (L-lactic acid) (PLLA), poly(glycolic acid) (PGA) or their copolymers, poly(DL-lactic-co-glycolic acid) (PLGA), and poly(ε-caprolactone) (PLC), poly(L-lactide) (LPLA), (DLPLA), poly(ε-caprolactone) (PCL), poly(dioxanone) (PDO), poly(glycolide-co-trimethylene carbonate) (PGA-TMC), poly(lactide-co-glycolide), poly-orthoesters, poly (anhydrides), polyhydroxybutyrate, poly (1-lactide-co-glycolide) (PGA-LPLA), cyanoacrylates, poly (L-lactide-co-glycolide) (PGA-DLPLA), poly(ethylene carbonate), poly(iminocarbonates), poly(1-lactide-co-dl-lactide) (LPLA-DLPLA), and poly(glycolide-co-trimethylene carbonate-co-dioxanone) (PDO-PGA-TMC).

Furthermore, at least a portion of the fixation devices of the present technology may be treated or coated with a calcium material, such as calcium deposits, calcium phosphate coatings, calcium sulfates, modified calcium salts such as Magnesium, Strontium and/or Silicon substituted calcium phosphates, RGD sequences, collagen, and combinations thereof in order to enhance a strength of bone ingrowth, on-growth, and/or through-growth between the segments or other portions of the fracture stabilization device.

CONCLUSION

Although many of the embodiments are described above with respect to implantable fixation devices, the technology is applicable to other applications and/or other approaches, such as non-implantable fixation devices. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1A-18B.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms "generally," "substantially," "about," and similar terms are used as terms of approximation and not as terms of degree, and are intended to account for the inherent variations in measured or calculated values that would be recognized by those of ordinary skill in the art.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A fixation device, comprising:

an elongate body comprising a plurality of interconnected segments, each of the segments comprising:

an engagement member, a recess configured to receive the engagement member of an adjacent one of the segments, the recess comprising a first portion and a second portion having a width greater than a width of the first portion, and a plurality of channels, wherein at least one of the channels extends through the engagement member; and a plurality of flexible elongate members, each extending through one of the channels, wherein the elongate body is transformable between a flexible configuration in which the elongate members can move relative to one another and a rigid configuration in which the elongate members are fixed relative to one another, and wherein the device is configured to transition from the flexible configuration to the rigid configuration via a locking mechanism that engages the elongate members to fix the elongate members relative to one another.

2. The device of claim 1, wherein the at least one of the channels is fully enclosed by at least a portion of the engagement member.

3. The device of claim 1, wherein at least one of the segments includes a plurality of engagement members.

4. The device of claim 1, wherein the engagement member comprises:

a neck extending away from an end face of the segment, and a broad portion extending away from the neck, wherein the broad portion comprises lateral surfaces and a top surface, and wherein a radius of curvature along the top surface is greater than a radius of curvature along the lateral surfaces.

5. The device of claim 1, wherein the engagement member comprises:

a neck extending away from an end face of the segment, and a broad portion extending away from the neck, the broad portion having a height to width ratio that is less than one.

6. The device of claim 1, wherein the engagement member comprises:

a neck extending away from an end face of the segment, and a broad portion extending away from the neck, wherein the broad portion comprises curved lateral sides and a substantially flat top side.

7. The device of claim 1, wherein each of the segments further comprises a lumen extending therethrough, wherein the lumen is configured to receive an elongate guide element.

8. The device of claim 1, wherein the elongate body is configured to be implanted within a patient.

9. The device of claim 1, wherein the elongate body is configured to be implanted in a bone of a patient.

10. The device of claim 1, wherein the elongate body is configured to be implanted within an intramedullary space of a bone of a patient.

11. A fixation device, comprising:

an elongate body comprising a plurality of interconnected segments, each of the segments comprising:

an engagement member, the engagement member comprising a first portion and a second portion having a width greater than a width of the first portion, a recess configured to receive the engagement member of an adjacent one of the segments, and a plurality of channels, wherein at least one of the channels is aligned along a circumferential dimension of the corresponding segment with the engagement member of the corresponding segment; and a plurality of flexible elongate members, each extending through one of the channels, wherein the elongate body is transformable between a flexible configuration in which the elongate members can move relative to one another and a rigid configuration in which the elongate members are fixed relative to one another, and wherein the device is configured to transition from the flexible configuration to the rigid configuration via a locking mechanism that engages the elongate members to fix the elongate members relative to one another.

12. The device of claim 11, wherein the at least one of the channels is fully enclosed by at least a portion of the engagement member.

13. The device of claim 11, wherein at least one of the segments includes a plurality of engagement members.

14. The device of claim 11, wherein the engagement member comprises:

a neck extending away from an end face of the segment, and a broad portion extending away from the neck, wherein the broad portion comprises lateral surfaces and a top surface, and wherein a radius of curvature along the top surface is greater than a radius of curvature along the lateral surfaces.

15. The device of claim 11, wherein the engagement member comprises:

a neck extending away from an end face of the segment, and a broad portion extending away from the neck, the broad portion having a height to width ratio that is less than one.

16. The device of claim 11, wherein the engagement member comprises:

a neck extending away from an end face of the segment, and a broad portion extending away from the neck, wherein the broad portion comprises curved lateral sides and a substantially flat top side.

17. The device of claim 11, wherein each of the segments further comprises a lumen extending therethrough, wherein the lumen is configured to receive an elongate guide element.

18. The device of claim 11, wherein the elongate body is configured to be implanted within a patient.

19. The device of claim 11, wherein the elongate body is configured to be implanted in a bone of a patient.

20. The device of claim 11, wherein the elongate body is configured to be implanted within an intramedullary space of a bone of a patient.

21. A fixation device, comprising:

an elongate body comprising a plurality of interconnected segments, each of the segments comprising:

an engagement member, a recess configured to receive the engagement member of an adjacent one of the segments, the recess comprising a first portion and a second portion having a width greater than a width of the first portion, and a plurality of channels; and a plurality of flexible elongate members, each extending through one of the channels, wherein a minimum width of the engagement member is greater than a diameter of the flexible elongate members, wherein the elongate body is transformable between a flexible configuration in which the elongate members can move relative to one another and a rigid configuration in which the elongate members are fixed relative to one another, and wherein the device is configured to transition from the flexible configuration to the rigid configuration via a locking mechanism that engages the elongate members to fix the elongate members relative to one another.

22. The device of claim 21, wherein at least one of the segments includes a plurality of engagement members.

23. The device of claim 21, wherein the engagement member comprises:

a neck extending away from an end face of the segment, and a broad portion extending away from the neck, wherein the broad portion comprises lateral surfaces and a top surface, and wherein a radius of curvature along the top surface is greater than a radius of curvature along the lateral surfaces.

24. The device of claim 21, wherein the engagement member comprises:

a neck extending away from an end face of the segment, and a broad portion extending away from the neck, the broad portion having a height to width ratio that is less than one.

25. The device of claim 21, wherein the engagement member comprises:

a neck extending away from an end face of the segment, and a broad portion extending away from the neck, wherein the broad portion comprises curved lateral sides and a substantially flat top side.

26. The device of claim 21, wherein each of the segments further comprises a lumen extending therethrough, wherein the lumen is configured to receive an elongate guide element.

27. The device of claim 21, wherein the elongate body is configured to be implanted within a patient.

28. The device of claim 21, wherein the elongate body is configured to be implanted in a bone of a patient.

29. The device of claim 21, wherein the elongate body is configured to be implanted within an intramedullary space of a bone of a patient.

30. A fixation device, comprising:

an elongate body comprising a plurality of interconnected segments, each of the segments comprising:

a body having a first end portion and a second end portion, the body having a recess at the first end portion;

an engagement member extending away from the second end portion of the body, wherein the engagement member is configured to be received within a recess of an adjacent one of the segments, and wherein the engagement member comprises:

a neck having a first end at the second end portion of the body and a second end, and a broad portion at the second end of the neck, wherein the broad portion comprises lateral sides and a top side, and wherein a radius of curvature of the broad portion along the top side is greater than a radius of curvature along the lateral sides, the broad portion having a width greater than a width of the neck; and a plurality of channels, wherein at least one of the channels extends through the engagement member and the body; and a plurality of flexible elongate members, each extending through one of the channels, wherein the elongate body is transformable between a flexible configuration in which the elongate members can move relative to one another and a rigid configuration in which the elongate members are fixed relative to one another, and wherein the device is configured to transition from the flexible configuration to the rigid configuration via a locking mechanism that engages the elongate members to fix the elongate members relative to one another.

31. The device of claim 30, wherein the engagement member is a first engagement member and the segment further comprises a second engagement member extending away from the second end portion of the body, and wherein the second engagement member is configured to be received within the recess of the adjacent one of the segments.

32. A fixation device, comprising:

an elongate body comprising a plurality of interconnected segments, each of the segments comprising:

a body having a first end portion and a second end portion, the body having a recess at the first end portion;

an engagement member extending away from the second end portion of the body, wherein the engagement member is configured to be received within a recess of an adjacent one of the segments, and wherein the engagement member comprises:

a neck having a first end at the second end portion of the body and a second end, and a broad portion at the second end of the neck, the broad portion having a height to width ratio that is less than one, the broad portion having a width greater than a width of the neck; and a plurality of channels, wherein at least one of the channels extends through the engagement member and the body; and a plurality of flexible elongate members, each extending through one of the channels, wherein the elongate body is transformable between a flexible configuration in which the elongate members can move relative to one another and a rigid configuration in which the elongate members are fixed relative to one another, and wherein the device is configured to transition from the flexible configuration to the rigid configuration via a locking mechanism that engages the elongate members to fix the elongate members relative to one another.

33. The device of claim 32, wherein the engagement member is a first engagement member and the segment further comprises a second engagement member extending away from the second end portion of the body, and wherein the second engagement member is configured to be received within the recess of the adjacent one of the segments.

34. A fixation device comprising:

an elongate body comprising a plurality of interconnected segments, each of the segments comprising:

a body having a first end portion and a second end portion, the body having a recess at the first end portion;

an engagement member extending away from the second end portion of the body, wherein the engagement member is configured to be received within a recess of an adjacent one of the segments, and wherein the engagement member comprises:

a neck having a first end at the second end portion of the body and a second end, and a broad portion at the second end of the neck, the broad portion having a width greater than a width of the neck, wherein the broad portion comprises curved lateral sides and a substantially flat top side; and a plurality of channels, wherein at least one of the channels extends through the engagement member and the body; and a plurality of flexible elongate members, each extending through one of the channels, wherein the elongate body is transformable between a flexible configuration in which the elongate members can move relative to one another and a rigid configuration in which the elongate members are fixed relative to one another, and wherein the device is configured to transition from the flexible configuration to the rigid configuration via a locking mechanism that engages the elongate members to fix the elongate members relative to one another.

35. The device of claim 34, wherein the engagement member is a first engagement member and the segment further comprises a second engagement member extending away from the second end portion of the body, and wherein the second engagement member is configured to be received within the recess of the adjacent one of the segments.

* * * * *